US012227583B2

(12) United States Patent
Liao et al.

(10) Patent No.: US 12,227,583 B2
(45) Date of Patent: Feb. 18, 2025

(54) ANTI-OX40 ANTIBODY, ANTIGEN-BINDING FRAGMENT THEREOF, AND THE PHARMACEUTICAL USE

(71) Applicant: Jiangsu Hengrui Medicine Co., Ltd., Jiangsu (CN)

(72) Inventors: Cheng Liao, Jiangsu (CN); Zupeng Xu, Jiangsu (CN); Jiahua Jiang, Jiangsu (CN); Xin Ye, Jiangsu (CN); Lianshan Zhang, Jiangsu (CN)

(73) Assignee: Jiangsu Hengrui Medicine Co., Ltd., Jiangsu (CN)

( * ) Notice: Subject to any disclaimer, the term of this patent is extended or adjusted under 35 U.S.C. 154(b) by 958 days.

(21) Appl. No.: 17/278,259

(22) PCT Filed: Sep. 25, 2019

(86) PCT No.: PCT/CN2019/107787
§ 371 (c)(1),
(2) Date: Mar. 19, 2021

(87) PCT Pub. No.: WO2020/063660
PCT Pub. Date: Apr. 2, 2020

(65) Prior Publication Data
US 2021/0355229 A1 Nov. 18, 2021

(30) Foreign Application Priority Data

Sep. 26, 2018 (CN) .......................... 201811128669.3
Nov. 26, 2018 (CN) .......................... 201811417666.1

(51) Int. Cl.
*C07K 16/28* (2006.01)
*A61K 39/00* (2006.01)
*A61P 35/00* (2006.01)

(52) U.S. Cl.
CPC .......... *C07K 16/2878* (2013.01); *A61P 35/00* (2018.01); *A61K 2039/505* (2013.01); *C07K 2317/24* (2013.01); *C07K 2317/565* (2013.01); *C07K 2317/567* (2013.01); *C07K 2317/92* (2013.01)

(58) Field of Classification Search
None
See application file for complete search history.

(56) References Cited

U.S. PATENT DOCUMENTS

| 4,683,195 | A | 7/1987 | Mullis et al. |
| 5,500,362 | A | 3/1996 | Robinson et al. |
| 5,821,337 | A | 10/1998 | Carter et al. |
| 6,194,551 | B1 | 2/2001 | Idusogie et al. |
| 6,737,056 | B1 | 5/2004 | Presta |
| 8,748,585 | B2 | 6/2014 | Attinger et al. |
| 9,644,032 | B2 | 5/2017 | Cai et al. |
| 10,442,866 | B1 | 10/2019 | Hu et al. |

FOREIGN PATENT DOCUMENTS

| CN | 107915775 A | 4/2018 |
| CN | 108137687 A | 6/2018 |
| CN | 110078825 A | 5/2020 |
| WO | 9951642 A1 | 10/1999 |
| WO | 2013038191 A2 | 3/2013 |
| WO | 2015153513 A1 | 10/2015 |
| WO | 2016179517 A1 | 11/2016 |
| WO | 2016196228 A1 | 12/2016 |
| WO | 2017096182 A1 | 6/2017 |

OTHER PUBLICATIONS

Thapta et al. Thapa, B., Kato, S., Nishizaki, D. et al. OX40/OX40 ligand and its role in precision immune oncology. Cancer Metastasis Rev (2024). https://doi.org/10.1007/s10555-024-10184-9 (Year: 2024).*
Merriam Webster definition: prevent. Accessed online May 8, 2024 (Year: 2024).*
Merriam Webster definition prophylactic. Accessed online May 8, 2024 (Year: 2024).*
Umar et al. Future directions in cancer prevention. Nat Rev Cancer 12, 835-848 (2012). (Year: 2012).*
Bode et al. Cancer prevention research—then and now. Nat Rev Cancer 9, 508-516 (Year: 2009).*
Sarfati et al. Preventing cancer: the only way forward. The Lancet. vol. 400, Iss: 10352, pp. 540-541 (Year: 2022).*
Kaczmarek et al. Cancer Vaccine Therapeutics: Limitations and Effectiveness—A Literature Review. Cells. 2023; 12(17):2159. (Year: 2023).*
Willoughby et al. (2017). OX40: Structure and function—What questions remain?. Molecular immunology, 83, 13-22 (Year: 2017).*
Fu et al. Therapeutic strategies for the costimulatory molecule OX40 in T-cell-mediated immunity. Acta Pharmaceutica Sinica B. 2020; 10(3):414-433 (Year: 2020).*
Thapta et al. Thapa, B., Kato, S., Nishizaki, D. et al. OX40/OX40 ligand and its role in precision immune oncology. Cancer Metastasis Rev. (Year: 2023).*
Merriam Webster definition: Derive. Accessed online May 8, 2024 (Year: 2024).*
Merriam Webster definitions: Variant: accessed online May 7, 2024 (Year: 2024).*
Merriam Webster definitions: Mutant: accessed online May 7, 2024 (Year: 2024).*

(Continued)

*Primary Examiner* — Daniel E Kolker
*Assistant Examiner* — Hilary Ann Petrash
(74) *Attorney, Agent, or Firm* — Taft Stettinius & Hollister LLP

(57) ABSTRACT

The present invention provides an anti-ox40 antibody, an antigen-binding fragment thereof, and the pharmaceutical use. Further, the present application provides a chimeric antibody and a humanized antibody, the chimeric antibody and the humanized antibody comprising a CDR region from the anti-OX40 antibody and the antigen-binding fragment thereof, and also provides a pharmaceutical composition comprising the anti-OX40 antibody and the antigen-binding fragment thereof, and the use thereof as a drug for treating cancers.

17 Claims, 3 Drawing Sheets

Specification includes a Sequence Listing.

(56) References Cited

OTHER PUBLICATIONS

David et al. A study of the structural correlates of affinity maturation: Antibody affinity as a function of chemical interactions, structural plasticity and stability. Molecular Immunology, 2007. 44: 1342-1351 (Year: 2007).*

Voo et al; Antibodies Targeting Human OX40 Expand Effector T Cells and Block Inducible and Natural Regulatory T Cell Function. J Immunol Oct. 1, 2013; 191 (7): 3641-3650. https://doi.org/10.4049/jimmunol.1202752 (Year: 2013).*

International Search Report; China National Intellectual Property Administration; International Application No. PCT/CN2019/107787; Dec. 26, 2019; 12 pages.

Sugamura, Kazuo et al.; Therapeutic targeting of the effector T-cell co-stimulatory molecule OX40; Nature Reviews Immunology; Jun. 2004; pp. 420-431; vol. 4.

Quezada, Sergio A. et al.; Shifting the equilibrium in cancer immunoediting: from tumor tolerance to eradication; Immunological Reviews; 2011; pp. 104-118; vol. 241; John Wiley & Sons A/S.

Sakaguchi, Shimon; Naturally Arising CD4+ Regulatory T Cells for Immunologic Self-Tolerance and Negative Control of Immune Responses; Annu. Rev. Immunol.; 2004; pp. 531-562; vol. 22.

Honjo, Tasuku et al.; Diphtheria Toxin-dependent Adenosine Diphosphate Ribosylation of Aminoacyl Transferase II and Inhibition of Protein Synthesis; J. Biol. Chem; Jun. 25, 1968; pp. 3553-3555; vol. 243; No. 12.

Ward, E. Sally et al.; Binding activities of a repertoire of single immunoglobulin variable domains secreted from *Escherichia coli*; Nature; Oct. 12, 1989; pp. 544-546; vol. 341; Nature Publishing Group.

Bird, Robert E.; Single-Chain Antigen-Binding Proteins; Science; Oct. 21, 1988; pp. 423-426; vol. 242.

Huston, James S. et al.; Protein engineering of antibody binding sites: Recovery of specific activity in an anti-digoxin single-chain Fv analogue produced in *Escherichia coli*; Proc. Natl. Acad. Sci. USA; Aug. 1988; pp. 5879-5883; vol. 85.

Holliger, Philipp et al.; "Diabodies": Small bivalent and bispecific antibody fragments; Proc. Natl. Acad. Sci. USA; Jul. 1993; pp. 6444-6448; vol. 90.

Alfthan, Kaija et al.; Properties of a single-chain antibody containing different linker peptides; Protein Engineering; 1995; pp. 725-731; vol. 8; No. 7; Oxford University Press.

Choi, Ingrid et al.; Recombinant chimeric OKT3 scFv IgM antibodies mediate immune suppression while reducing T cell activation in vitro; Eur. J. Immunol.; 2001; pp. 94-106; vol. 31; WILEY-VCH Verlag GmbH.

Hu, Shu-zhen et al.; Minibody: A Novel Engineered Anti-Carcinoembryonic Antigen Antibody Fragment (Single-Chain Fv-CH3) Which Exhibits Rapid, High-Level Targeting of Xenografts; Cancer Research; Jul. 1, 1996; pp. 3055-3061; vol. 56; American Association for Cancer Research.

Kipriyanov, Sergey et al.; Bispecific Tandem Diabody for Tumor Therapy with Improved Antigen Binding and Pharmacokinetics; J. Mol. Biol.; 1999; pp. 41-56; vol. 293; Academic Press.

Roovers, Rob. C. et al.; In vito characterisation of a monovalent and bivalent form of a fully human anti Ep-CAM phage antibody; Cancer Immunol Immunother; 2001; pp. 51-59; vol. 50; Springer-Verlag.

Reiter, Yoram et al.; Engineering interchain disulfide bonds into conserved framework regions of Fv fragments: improved biochemical characteristics of recombinant immunotoxins containing disulfide-stabilized Fv; Protein Engineering; 1994; pp. 697-704; vol. 7; No. 5.

Kirkland, Theo N. et al.; Analysis of fine specificity and cross-reactivity of monoclonal antilipid A antibodies; The Journal of Immunology; Dec. 1, 1986; pp. 3614-3619; vol. 137; No. 11; The American Association of Immunologists, Inc.

Harlow, Ed et al.; Antibodies: A Laboratory Manual; 1988; 2 pages; Cold Spring Harbor Laboratory.

Morel, Guillemette A. et al.; Monoclonal antibodies to bovine serum albumin: Affinity and specificity determinations; Molecular Immunology; 1988; pp. 7-15; vol. 25; No. 1; Pergamon Journals Ltd.

Moldenhauer, G. et al.; Identity of HML-1 Antigen on Intestinal Intraepithelial T Cells and of B-ly7 Antigen on Hairy Cell Leukaemia; Scand. J. Immunol.; 1990; pp. 77-82; vol. 32.

Ravetch, Jeffrey V. et al.; Fc receptors; Annu. Rev. Immunol.; 1991; pp. 457-492; vol. 9; Annual Reviews Inc.

Clynes, Raphael et al.; Fc receptors are required in passive and active immunity to melanoma; Proc. Natl. Acad. Sci. USA; Jan. 1998; pp. 652-656; vol. 95; The National Academy of Sciences.

Gazzano-Santoro, Hélène et al.; A non-radioactive complement-dependent cytotoxicity assay for anti-CD20 monoclonal antibody; Journal of Immunological Methods; 1997; pp. 163-171; vol. 202; Elsevier Science B.V.

Idusogie, Esohe et al.; Mapping of the C1q Binding Site on Rituxan, a Chimeric Antibody with a Human IgG1 Fc; The Journal of Immunology; 2000; pp. 4178-4184; vol. 164; The American Association of Immunologists, Inc.

Watson, J. D. et al.; Book Reviews: Molecular Biology of the Gene (Fourth Edition); General Principles; 1987; 1 page; vol. 1; The Benjamin/Cummings Publishing Company, Inc.

Mullis, F. et al.; Specific Enzymatic Amplification of DNA In Vitro: The Polymerase Chain Reaction; Cold Spring Harbor Symposia on Quantitative Biology; 1986; pp. 263-273; vol. LI; Cold Spring Harbor Laboratory.

Written Opinion of the International Searching Authority: China National Intellectual Property Administration; International Application No. PCT/CN2019/107787; Dec. 26, 2019; 12 pages.

Stähli, C. et al.; Distinction of Epitopes by Monoclonal Antibodies; Methods in Enzymology; 1983; pp. 242-253; vol. 92; Academic Press, Inc.

International Preliminary Report on Patentability; The International Bureau of WIPO; International Application No. PCT/CN2019/107787; Mar. 23, 2021; 12 pages.

\* cited by examiner

SEQUENCE LISTING

```
<160> NUMBER OF SEQ ID NOS: 42

<210> SEQ ID NO 1
<211> LENGTH: 113
<212> TYPE: PRT
<213> ORGANISM: Artificial Sequence
<220> FEATURE:
<221> NAME/KEY: DOMAIN
<222> LOCATION: (1)..(113)
<223> OTHER INFORMATION: Heavy chain variable region of Murine
      monoclonal antibody m4B5

<400> SEQUENCE: 1

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Ser Tyr
            20                  25                  30

Gly Leu His Trp Phe Arg Gln Ser Pro Gly Lys Gly Leu Glu Trp Leu
        35                  40                  45

Gly Val Ile Trp Ser Gly Gly Ser Thr Asp Tyr Asn Ala Ala Phe Ile
    50                  55                  60

Ser Arg Leu Ser Ile Ser Lys Asp Asp Ser Lys Ser Gln Val Phe Phe
65                  70                  75                  80

Lys Met Asn Ser Leu Gln Ala Asp Asp Thr Ala Ile Tyr Tyr Cys Ala
                85                  90                  95

Arg Glu Glu Tyr Asp Val Trp Gly Thr Gly Thr Thr Val Thr Val Ser
            100                 105                 110

Ser

<210> SEQ ID NO 2
<211> LENGTH: 107
<212> TYPE: PRT
<213> ORGANISM: Artificial Sequence
<220> FEATURE:
<221> NAME/KEY: DOMAIN
<222> LOCATION: (1)..(107)
<223> OTHER INFORMATION: Light chain variable region of Murine
      monoclonal antibody m4B5

<400> SEQUENCE: 2

Asp Ile Gln Met Thr Gln Thr Ala Ser Ser Leu Ser Ala Ser Leu Gly
```

```
                1               5                  10                 15
Asp Arg Val Thr Ile Ser Cys Arg Ala Ser Gln Asp Ile Ser Asn Tyr
                20                 25                 30

Leu Asn Trp Tyr Gln Gln Lys Pro Asp Gly Thr Val Lys Leu Leu Ile
        35                 40                 45

Tyr Tyr Thr Ser Arg Leu His Ser Gly Val Pro Ser Arg Phe Ser Gly
        50                 55                 60

Ser Gly Ser Gly Thr Asp Tyr Ser Leu Thr Ile Ser Asn Leu Glu Gln
65                 70                 75                 80

Glu Asp Val Ala Thr Tyr Phe Cys Gln Gln Gly Asn Thr Leu Pro Trp
                85                 90                 95

Thr Phe Gly Gly Gly Thr Lys Leu Glu Ile Lys
            100                 105

<210> SEQ ID NO 3
<211> LENGTH: 5
<212> TYPE: PRT
<213> ORGANISM: Artificial Sequence
<220> FEATURE:
<221> NAME/KEY: DOMAIN
<222> LOCATION: (1)..(5)
<223> OTHER INFORMATION: HCDR1 of Murine monoclonal antibody m4B5

<400> SEQUENCE: 3

Ser Tyr Gly Leu His
1               5

<210> SEQ ID NO 4
<211> LENGTH: 16
<212> TYPE: PRT
<213> ORGANISM: Artificial Sequence
<220> FEATURE:
<221> NAME/KEY: DOMAIN
<222> LOCATION: (1)..(16)
<223> OTHER INFORMATION: HCDR2 of Murine monoclonal antibody m4B5

<400> SEQUENCE: 4

Val Ile Trp Ser Gly Gly Ser Thr Asp Tyr Asn Ala Ala Phe Ile Ser
1               5                  10                 15

<210> SEQ ID NO 5
<211> LENGTH: 5
<212> TYPE: PRT
<213> ORGANISM: Artificial Sequence
<220> FEATURE:
<221> NAME/KEY: DOMAIN
<222> LOCATION: (1)..(5)
<223> OTHER INFORMATION: HCDR3 of Murine monoclonal antibody m4B5

<400> SEQUENCE: 5

Glu Glu Tyr Asp Val
1               5

<210> SEQ ID NO 6
<211> LENGTH: 11
<212> TYPE: PRT
<213> ORGANISM: Artificial Sequence
<220> FEATURE:
<221> NAME/KEY: DOMAIN
<222> LOCATION: (1)..(11)
<223> OTHER INFORMATION: LCDR1 of Murine monoclonal antibody m4B5

<400> SEQUENCE: 6

Arg Ala Ser Gln Asp Ile Ser Asn Tyr Leu Asn
1               5                  10
```

<210> SEQ ID NO 7
<211> LENGTH: 7
<212> TYPE: PRT
<213> ORGANISM: Artificial Sequence
<220> FEATURE:
<221> NAME/KEY: DOMAIN
<222> LOCATION: (1)..(7)
<223> OTHER INFORMATION: LCDR2 of Murine monoclonal antibody m4B5

<400> SEQUENCE: 7

Tyr Thr Ser Arg Leu His Ser
1               5

<210> SEQ ID NO 8
<211> LENGTH: 9
<212> TYPE: PRT
<213> ORGANISM: Artificial Sequence
<220> FEATURE:
<221> NAME/KEY: DOMAIN
<222> LOCATION: (1)..(9)
<223> OTHER INFORMATION: LCDR3 of Murine monoclonal antibody m4B5

<400> SEQUENCE: 8

Gln Gln Gly Asn Thr Leu Pro Trp Thr
1               5

<210> SEQ ID NO 9
<211> LENGTH: 119
<212> TYPE: PRT
<213> ORGANISM: Artificial Sequence
<220> FEATURE:
<221> NAME/KEY: DOMAIN
<222> LOCATION: (1)..(119)
<223> OTHER INFORMATION: Heavy chain variable region of Murine
      monoclonal antibody m2G3

<400> SEQUENCE: 9

Gln Val Gln Leu Lys Glu Ser Gly Pro Gly Leu Val Ala Ser Ser Gln
1               5                   10                  15

Ser Leu Ser Ile Thr Cys Thr Val Ser Gly Phe Ser Leu Ser Arg Tyr
            20                  25                  30

Ser Val His Trp Val Arg Gln Pro Pro Gly Lys Gly Leu Glu Trp Leu
        35                  40                  45

Gly Met Ile Trp Asp Gly Gly Asn Thr Asp Tyr Asn Ser Ala Leu Lys
    50                  55                  60

Ser Arg Leu Ser Ile Ser Lys Asp Asn Ser Lys Ser Gln Val Phe Leu
65                  70                  75                  80

Lys Met Asn Ser Leu Gln Thr Asp Asp Thr Ala Met Tyr Tyr Cys Ala
                85                  90                  95

Arg Asn Pro Leu Tyr Phe Ser Tyr Ala Met Asp Tyr Trp Gly Gln Gly
            100                 105                 110

Thr Ser Val Thr Val Ser Ser
        115

<210> SEQ ID NO 10
<211> LENGTH: 107
<212> TYPE: PRT
<213> ORGANISM: Artificial Sequence
<220> FEATURE:
<221> NAME/KEY: DOMAIN
<222> LOCATION: (1)..(107)
<223> OTHER INFORMATION: Light chain variable region of Murine
      monoclonal antibody m2G3

<400> SEQUENCE: 10

Asp Ile Gln Met Thr Gln Ser Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Ile Tyr Thr Ser Arg Leu Gln Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Val Asn Thr Phe Pro Phe
                85                  90                  95

Thr Phe Gly Ser Gly Thr Lys Leu Glu Ile Lys
            100                 105

<210> SEQ ID NO 11
<211> LENGTH: 5
<212> TYPE: PRT
<213> ORGANISM: Artificial Sequence
<220> FEATURE:
<221> NAME/KEY: DOMAIN
<222> LOCATION: (1)..(5)
<223> OTHER INFORMATION: HCDR1 of Murine monoclonal antibody m2G3

<400> SEQUENCE: 11

Arg Tyr Ser Val His
1               5

<210> SEQ ID NO 12
<211> LENGTH: 16
<212> TYPE: PRT
<213> ORGANISM: Artificial Sequence
<220> FEATURE:
<221> NAME/KEY: DOMAIN
<222> LOCATION: (1)..(16)
<223> OTHER INFORMATION: HCDR2 of Murine monoclonal antibody m2G3

<400> SEQUENCE: 12

Met Ile Trp Asp Gly Gly Asn Thr Asp Tyr Asn Ser Ala Leu Lys Ser
1               5                   10                  15

<210> SEQ ID NO 13
<211> LENGTH: 11
<212> TYPE: PRT
<213> ORGANISM: Artificial Sequence
<220> FEATURE:
<221> NAME/KEY: DOMAIN
<222> LOCATION: (1)..(11)
<223> OTHER INFORMATION: HCDR3 of Murine monoclonal antibody m2G3

<400> SEQUENCE: 13

Asn Pro Leu Tyr Phe Ser Tyr Ala Met Asp Tyr
1               5                   10

<210> SEQ ID NO 14
<211> LENGTH: 11
<212> TYPE: PRT
<213> ORGANISM: Artificial Sequence
<220> FEATURE:
<221> NAME/KEY: DOMAIN
<222> LOCATION: (1)..(11)
<223> OTHER INFORMATION: LCDR1 of Murine monoclonal antibody m2G3

<400> SEQUENCE: 14

Arg Ala Ser Gln Asp Ile Ser Asn Tyr Leu Asn
1               5                   10

<210> SEQ ID NO 15
<211> LENGTH: 7
<212> TYPE: PRT
<213> ORGANISM: Artificial Sequence
<220> FEATURE:
<221> NAME/KEY: DOMAIN
<222> LOCATION: (1)..(7)
<223> OTHER INFORMATION: LCDR2 of Murine monoclonal antibody m2G3

<400> SEQUENCE: 15

Tyr Thr Ser Arg Leu Gln Ser
1               5

<210> SEQ ID NO 16
<211> LENGTH: 9
<212> TYPE: PRT
<213> ORGANISM: Artificial Sequence
<220> FEATURE:
<221> NAME/KEY: DOMAIN
<222> LOCATION: (1)..(9)
<223> OTHER INFORMATION: LCDR3 of Murine monoclonal antibody m2G3

<400> SEQUENCE: 16

Gln Gln Val Asn Thr Phe Pro Phe Thr
1               5

<210> SEQ ID NO 17
<211> LENGTH: 119
<212> TYPE: PRT
<213> ORGANISM: Artificial Sequence
<220> FEATURE:
<221> NAME/KEY: DOMAIN
<222> LOCATION: (1)..(119)
<223> OTHER INFORMATION: Heavy chain variable region VH1 of humanized
    mAb hu2G3

<400> SEQUENCE: 17

Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Ser Arg Tyr
            20                  25                  30

Ser Val His Trp Val Arg Gln Pro Pro Gly Lys Gly Leu Glu Trp Ile
        35                  40                  45

Gly Met Ile Trp Asp Gly Gly Asn Thr Asp Tyr Asn Ser Ala Leu Lys
    50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asn Pro Leu Tyr Phe Ser Tyr Ala Met Asp Tyr Trp Gly Gln Gly
            100                 105                 110

Thr Leu Val Thr Val Ser Ser
        115

<210> SEQ ID NO 18
<211> LENGTH: 119
<212> TYPE: PRT
<213> ORGANISM: Artificial Sequence
<220> FEATURE:
<221> NAME/KEY: DOMAIN
<222> LOCATION: (1)..(119)

<223> OTHER INFORMATION: Heavy chain variable region VH2 of humanized
    mAb hu2G3

<400> SEQUENCE: 18

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Arg Tyr
            20                  25                  30

Ser Val His Trp Ile Arg Gln Pro Pro Gly Lys Gly Leu Glu Trp Ile
        35                  40                  45

Gly Met Ile Trp Asp Gly Gly Asn Thr Asp Tyr Asn Ser Ala Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asn Pro Leu Tyr Phe Ser Tyr Ala Met Asp Tyr Trp Gly Gln Gly
            100                 105                 110

Thr Leu Val Thr Val Ser Ser
        115

<210> SEQ ID NO 19
<211> LENGTH: 107
<212> TYPE: PRT
<213> ORGANISM: Artificial Sequence
<220> FEATURE:
<221> NAME/KEY: DOMAIN
<222> LOCATION: (1)..(107)
<223> OTHER INFORMATION: Light chain variable region VL1 of humanized
    mAb hu2G3

<400> SEQUENCE: 19

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Asp Gln Ser Pro Lys Leu Leu Ile
        35                  40                  45

Ile Tyr Thr Ser Arg Leu Gln Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Val Asn Thr Phe Pro Phe
                85                  90                  95

Thr Phe Gly Gln Gly Thr Lys Leu Glu Ile Lys
            100                 105

<210> SEQ ID NO 20
<211> LENGTH: 107
<212> TYPE: PRT
<213> ORGANISM: Artificial Sequence
<220> FEATURE:
<221> NAME/KEY: DOMAIN
<222> LOCATION: (1)..(107)
<223> OTHER INFORMATION: Light chain variable region VL2 of humanized
    mAb hu2G3

<400> SEQUENCE: 20

Asp Ile Gln Met Thr Gln Ser Pro Ser Ser Leu Ser Ala Ser Val Gly
1               5                   10                  15

```
Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Gln Ser Gly Val Pro Ser Arg Phe Ser Gly
    50                  55                  60

Ser Gly Ser Gly Thr Asp Tyr Thr Leu Thr Ile Ser Ser Leu Gln Pro
 65                 70                  75                  80

Glu Asp Phe Ala Thr Tyr Tyr Cys Gln Gln Val Asn Thr Phe Pro Phe
                85                  90                  95

Thr Phe Gly Gln Gly Thr Lys Leu Glu Ile Lys
            100                 105
```

<210> SEQ ID NO 21
<211> LENGTH: 107
<212> TYPE: PRT
<213> ORGANISM: Artificial Sequence
<220> FEATURE:
<221> NAME/KEY: DOMAIN
<222> LOCATION: (1)..(107)
<223> OTHER INFORMATION: Light chain variable region VL0 of humanized
      mAb hu4B5

<400> SEQUENCE: 21

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Val Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro
 65                 70                  75                  80

Glu Asp Val Ala Thr Tyr Tyr Cys Gln Gln Gly Asn Thr Leu Pro Trp
                85                  90                  95

Thr Phe Gly Gly Gly Thr Lys Val Glu Ile Lys
            100                 105
```

<210> SEQ ID NO 22
<211> LENGTH: 107
<212> TYPE: PRT
<213> ORGANISM: Artificial Sequence
<220> FEATURE:
<221> NAME/KEY: DOMAIN
<222> LOCATION: (1)..(107)
<223> OTHER INFORMATION: Light chain variable region VL1 of humanized
      mAb hu4B5

<400> SEQUENCE: 22

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Val Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
 65                 70                  75                  80
```

```
Glu Asp Val Ala Thr Tyr Tyr Cys Gln Gln Gly Asn Thr Leu Pro Trp
                85                  90                  95

Thr Phe Gly Gly Gly Thr Lys Val Glu Ile Lys
            100                 105

<210> SEQ ID NO 23
<211> LENGTH: 107
<212> TYPE: PRT
<213> ORGANISM: Artificial Sequence
<220> FEATURE:
<221> NAME/KEY: DOMAIN
<222> LOCATION: (1)..(107)
<223> OTHER INFORMATION: Light chain variable region VL2 of humanized
      mAb hu4B5

<400> SEQUENCE: 23

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Gly Val Pro Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Val Ala Thr Tyr Tyr Cys Gln Gln Gly Asn Thr Leu Pro Trp
                85                  90                  95

Thr Phe Gly Gly Gly Thr Lys Val Glu Ile Lys
            100                 105

<210> SEQ ID NO 24
<211> LENGTH: 107
<212> TYPE: PRT
<213> ORGANISM: Artificial Sequence
<220> FEATURE:
<221> NAME/KEY: DOMAIN
<222> LOCATION: (1)..(107)
<223> OTHER INFORMATION: Light chain variable region VL3 of humanized
      mAb hu4B5

<400> SEQUENCE: 24

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Gly Val Pro Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Tyr Thr Leu Thr Ile Ser Ser Leu Gln Gln
65                  70                  75                  80

Glu Asp Val Ala Thr Tyr Tyr Cys Gln Gln Gly Asn Thr Leu Pro Trp
                85                  90                  95

Thr Phe Gly Gly Gly Thr Lys Val Glu Ile Lys
            100                 105

<210> SEQ ID NO 25
<211> LENGTH: 107
<212> TYPE: PRT
```

```
<213> ORGANISM: Artificial Sequence
<220> FEATURE:
<221> NAME/KEY: DOMAIN
<222> LOCATION: (1)..(107)
<223> OTHER INFORMATION: Light chain variable region VL4 of humanized
      mAb hu4B5

<400> SEQUENCE: 25

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Gly Thr Val Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Val Ala Thr Tyr Phe Cys Gln Gln Gly Asn Thr Leu Pro Trp
                85                  90                  95

Thr Phe Gly Gly Gly Thr Lys Val Glu Ile Lys
            100                 105

<210> SEQ ID NO 26
<211> LENGTH: 113
<212> TYPE: PRT
<213> ORGANISM: Artificial Sequence
<220> FEATURE:
<221> NAME/KEY: DOMAIN
<222> LOCATION: (1)..(113)
<223> OTHER INFORMATION: Heavy chain variable region VH0 of humanized
      mAb hu4B5

<400> SEQUENCE: 26

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

Gly Leu His Trp Ile Arg Gln Pro Pro Gly Lys Gly Leu Glu Trp Ile
        35                  40                  45

Gly Val Ile Trp Ser Gly Gly Ser Thr Asp Tyr Asn Ala Ala Phe Ile
50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Glu Tyr Asp Val Trp Gly Gln Gly Thr Thr Val Thr Val Ser
            100                 105                 110

Ser

<210> SEQ ID NO 27
<211> LENGTH: 113
<212> TYPE: PRT
<213> ORGANISM: Artificial Sequence
<220> FEATURE:
<221> NAME/KEY: DOMAIN
<222> LOCATION: (1)..(113)
<223> OTHER INFORMATION: Heavy chain variable region VH1 of humanized
      mAb hu4B5

<400> SEQUENCE: 27
```

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

Gly Leu His Trp Ile Arg Gln Pro Pro Gly Lys Gly Leu Glu Trp Ile
        35                  40                  45

Gly Val Ile Trp Ser Gly Gly Ser Thr Asp Tyr Asn Ala Ala Phe Ile
    50                  55                  60

Ser Arg Val Thr Ile Ser Lys Glu Asp Ser Lys Asn Gln Phe Ser Leu
65                  70                  75                  80

Lys Leu Ser Ser Val Thr Ala Ala Asp Thr Ala Val Tyr Tyr Cys Ala
            85                  90                  95

Arg Glu Glu Tyr Asp Val Trp Gly Gln Gly Thr Thr Val Thr Val Ser
            100                 105                 110

Ser
```

<210> SEQ ID NO 28
<211> LENGTH: 113
<212> TYPE: PRT
<213> ORGANISM: Artificial Sequence
<220> FEATURE:
<221> NAME/KEY: DOMAIN
<222> LOCATION: (1)..(113)
<223> OTHER INFORMATION: Heavy chain variable region VH2 of humanized mAb hu4B5

<400> SEQUENCE: 28

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

Gly Leu His Trp Ile Arg Gln Pro Pro Gly Lys Gly Leu Glu Trp Ile
        35                  40                  45

Gly Val Ile Trp Ser Gly Gly Ser Thr Asp Tyr Asn Ala Ala Phe Ile
    50                  55                  60

Ser Arg Val Thr Ile Ser Lys Glu Asp Ser Lys Ser Gln Val Ser Leu
65                  70                  75                  80

Lys Leu Ser Ser Val Thr Ala Ala Asp Thr Ala Val Tyr Tyr Cys Ala
            85                  90                  95

Arg Glu Glu Tyr Asp Val Trp Gly Gln Gly Thr Thr Val Thr Val Ser
            100                 105                 110

Ser
```

<210> SEQ ID NO 29
<211> LENGTH: 113
<212> TYPE: PRT
<213> ORGANISM: Artificial Sequence
<220> FEATURE:
<221> NAME/KEY: DOMAIN
<222> LOCATION: (1)..(113)
<223> OTHER INFORMATION: Heavy chain variable region VH3 of humanized mAb hu4B5

<400> SEQUENCE: 29

```
Gln Val Gln Leu Lys Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

Gly Leu His Trp Phe Arg Gln Pro Pro Gly Lys Gly Leu Glu Trp Ile
```

```
                    35                  40                  45
Gly Val Ile Trp Ser Gly Gly Ser Thr Asp Tyr Asn Ala Ala Phe Ile
             50                  55                  60
Ser Arg Val Thr Ile Ser Lys Glu Asp Ser Lys Ser Gln Val Ser Leu
 65                  70                  75                  80
Lys Leu Ser Ser Val Thr Ala Ala Asp Thr Ala Val Tyr Tyr Cys Ala
                 85                  90                  95
Arg Glu Glu Tyr Asp Val Trp Gly Gln Gly Thr Thr Val Thr Val Ser
                100                 105                 110
Ser

<210> SEQ ID NO 30
<211> LENGTH: 113
<212> TYPE: PRT
<213> ORGANISM: Artificial Sequence
<220> FEATURE:
<221> NAME/KEY: DOMAIN
<222> LOCATION: (1)..(113)
<223> OTHER INFORMATION: Heavy chain variable region VH4 of humanized
      mAb hu4B5

<400> SEQUENCE: 30

Gln Val Gln Leu Lys Glu Ser Gly Pro Gly Leu Val Lys Pro Ser Glu
 1               5                  10                  15
Thr Leu Ser Leu Thr Cys Thr Val Ser Gly Phe Ser Leu Thr Ser Tyr
                20                  25                  30
Gly Leu His Trp Phe Arg Gln Pro Pro Gly Lys Gly Leu Glu Trp Leu
             35                  40                  45
Gly Val Ile Trp Ser Gly Gly Ser Thr Asp Tyr Asn Ala Ala Phe Ile
             50                  55                  60
Ser Arg Leu Thr Ile Ser Lys Glu Asp Ser Lys Ser Gln Val Ser Leu
 65                  70                  75                  80
Lys Leu Ser Ser Val Thr Ala Ala Asp Thr Ala Val Tyr Tyr Cys Ala
                 85                  90                  95
Arg Glu Glu Tyr Asp Val Trp Gly Gln Gly Thr Thr Val Thr Val Ser
                100                 105                 110
Ser

<210> SEQ ID NO 31
<211> LENGTH: 119
<212> TYPE: PRT
<213> ORGANISM: Artificial Sequence
<220> FEATURE:
<221> NAME/KEY: DOMAIN
<222> LOCATION: (1)..(119)
<223> OTHER INFORMATION: Heavy chain variable region VH1.1 of humanized
      mAb hu2G3

<400> SEQUENCE: 31

Gln Val Gln Leu Gln Glu Ser Gly Pro Gly Leu Val Lys Pro Ser Glu
 1               5                  10                  15
Thr Leu Ser Leu Thr Cys Thr Val Ser Gly Tyr Ser Ile Ser Arg Tyr
                20                  25                  30
Ser Val His Trp Val Arg Gln Pro Pro Gly Lys Gly Leu Glu Trp Ile
             35                  40                  45
Gly Met Ile Trp Asp Gly Gly Asn Thr Asp Tyr Asn Ala Ala Leu Lys
             50                  55                  60
Ser Arg Phe Thr Ile Ser Arg Asp Asn Ala Lys Asn Thr Leu Tyr Leu
 65                  70                  75                  80
```

Gln Met Asn Ser Leu Arg Ala Glu Asp Thr Ala Val Tyr Tyr Cys Ala
                85                  90                  95

Arg Asn Pro Leu Tyr Phe Ser Tyr Ala Met Asp Tyr Trp Gly Gln Gly
            100                 105                 110

Thr Leu Val Thr Val Ser Ser
        115

<210> SEQ ID NO 32
<211> LENGTH: 119
<212> TYPE: PRT
<213> ORGANISM: Artificial Sequence
<220> FEATURE:
<221> NAME/KEY: DOMAIN
<222> LOCATION: (1)..(119)
<223> OTHER INFORMATION: Heavy chain variable region VH1.2 of humanized
      mAb hu2G3

<400> SEQUENCE: 32

Gln Val Gln Leu Gln Glu Ser Gly Pro Gly Leu Val Lys Pro Ser Gln
1               5                   10                  15

Thr Leu Ser Leu Thr Cys Thr Val Ser Gly Phe Ser Leu Ser Arg Tyr
            20                  25                  30

Ser Val His Trp Val Arg Gln Pro Pro Gly Lys Gly Leu Glu Trp Ile
        35                  40                  45

Gly Met Ile Trp Asp Gly Gly Asn Thr Asp Tyr Ala Ala Pro Val Lys
    50                  55                  60

Gly Arg Phe Thr Ile Ser Arg Asp Asp Ser Lys Asn Thr Leu Tyr Leu
65                  70                  75                  80

Gln Met Asn Ser Leu Lys Thr Glu Asp Thr Ala Val Tyr Tyr Cys Ala
                85                  90                  95

Arg Asn Pro Leu Tyr Phe Ser Tyr Ala Met Asp Tyr Trp Gly Gln Gly
            100                 105                 110

Thr Leu Val Thr Val Ser Ser
        115

<210> SEQ ID NO 33
<211> LENGTH: 16
<212> TYPE: PRT
<213> ORGANISM: Artificial Sequence
<220> FEATURE:
<221> NAME/KEY: DOMAIN
<222> LOCATION: (1)..(16)
<223> OTHER INFORMATION: HCDR2V1 of mAb hu2G3

<400> SEQUENCE: 33

Met Ile Trp Asp Gly Gly Asn Thr Asp Tyr Asn Ala Ala Leu Lys Ser
1               5                   10                  15

<210> SEQ ID NO 34
<211> LENGTH: 16
<212> TYPE: PRT
<213> ORGANISM: Artificial Sequence
<220> FEATURE:
<221> NAME/KEY: DOMAIN
<222> LOCATION: (1)..(16)
<223> OTHER INFORMATION: HCDR2V2 of mAb hu2G3

<400> SEQUENCE: 34

Met Ile Trp Asp Gly Gly Asn Thr Asp Tyr Ala Ala Pro Val Lys Gly
1               5                   10                  15

<210> SEQ ID NO 35

```
<211> LENGTH: 330
<212> TYPE: PRT
<213> ORGANISM: Artificial Sequence
<220> FEATURE:
<221> NAME/KEY: DOMAIN
<222> LOCATION: (1)..(330)
<223> OTHER INFORMATION: IgG1 heavy chain constant region

<400> SEQUENCE: 35

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 36
<211> LENGTH: 107
<212> TYPE: PRT
<213> ORGANISM: Artificial Sequence
<220> FEATURE:
```

```
<221> NAME/KEY: DOMAIN
<222> LOCATION: (1)..(107)
<223> OTHER INFORMATION: kappa light chain constant region

<400> SEQUENCE: 36

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 37
<211> LENGTH: 449
<212> TYPE: PRT
<213> ORGANISM: Artificial Sequence
<220> FEATURE:
<221> NAME/KEY: CHAIN
<222> LOCATION: (1)..(449)
<223> OTHER INFORMATION: Heavy chain of Antibody 2G3

<400> SEQUENCE: 37

Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Ser Arg Tyr
            20                  25                  30

Ser Val His Trp Val Arg Gln Pro Pro Gly Lys Gly Leu Glu Trp Ile
        35                  40                  45

Gly Met Ile Trp Asp Gly Gly Asn Thr Asp Tyr Asn Ala Ala Leu Lys
    50                  55                  60

Ser Arg Phe Thr Ile Ser Arg Asp Asn Ala Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asn Pro Leu Tyr Phe Ser Tyr Ala Met Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
```

```
                        210                 215                 220
Thr His Thr Cys Pro Pro Cys Pro Ala Pro Glu Leu Gly Gly Pro
225                 230                 235                 240

Ser Val Phe Leu Phe Pro Pro Lys Pro Lys Asp Thr Leu Met Ile Ser
                    245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                    325                 330                 335

Thr Ile Ser Lys Ala Lys Gly Gln Pro Arg Glu Pro Gln Val Tyr Thr
                340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                    405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445

Lys

<210> SEQ ID NO 38
<211> LENGTH: 214
<212> TYPE: PRT
<213> ORGANISM: Artificial Sequence
<220> FEATURE:
<221> NAME/KEY: CHAIN
<222> LOCATION: (1)..(214)
<223> OTHER INFORMATION: Light chain of antibody 2G3

<400> SEQUENCE: 38

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Asp Gln Ser Pro Lys Leu Leu Ile
        35                  40                  45

Ile Tyr Thr Ser Arg Leu Gln Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Val Asn Thr Phe Pro Phe
                85                  90                  95

Thr Phe Gly Gln Gly Thr Lys Leu Glu Ile Lys Arg Thr Val Ala Ala
            100                 105                 110
```

```
Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210
```

<210> SEQ ID NO 39
<211> LENGTH: 443
<212> TYPE: PRT
<213> ORGANISM: Artificial Sequence
<220> FEATURE:
<221> NAME/KEY: CHAIN
<222> LOCATION: (1)..(443)
<223> OTHER INFORMATION: Heavy chain of antibody 4B5

<400> SEQUENCE: 39

```
Gln Val Gln Leu Lys Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

Gly Leu His Trp Phe Arg Gln Pro Pro Gly Lys Gly Leu Glu Trp Ile
        35                  40                  45

Gly Val Ile Trp Ser Gly Gly Ser Thr Asp Tyr Asn Ala Ala Phe Ile
    50                  55                  60

Ser Arg Val Thr Ile Ser Lys Glu Asp Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Arg Glu Glu Tyr Asp Val Trp Gly Gln Gly Thr Thr Val Thr Val Ser
            100                 105                 110

Ser Ala Ser Thr Lys Gly Pro Ser Val Phe Pro Leu Ala Pro Ser Ser
        115                 120                 125

Lys Ser Thr Ser Gly Gly Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
        195                 200                 205

Lys Lys Val Glu Pro Lys Ser Cys Asp Lys Thr His Thr Cys Pro Pro
    210                 215                 220

Cys Pro Ala Pro Glu Leu Leu Gly Gly Pro Ser Val Phe Leu Phe Pro
225                 230                 235                 240

Pro Lys Pro Lys Asp Thr Leu Met Ile Ser Arg Thr Pro Glu Val Thr
```

```
                        245                 250                 255
        Cys Val Val Asp Val Ser His Glu Asp Pro Glu Val Lys Phe Asn
                    260                 265                 270

Trp Tyr Val Asp Gly Val Glu Val His Asn Ala Lys Thr Lys Pro Arg
                275                 280                 285

Glu Glu Gln Tyr Asn Ser Thr Tyr Arg Val Val Ser Val Leu Thr Val
                290                 295                 300

Leu His Gln Asp Trp Leu Asn Gly Lys Glu Tyr Lys Cys Lys Val Ser
        305                 310                 315                 320

Asn Lys Ala Leu Pro Ala Pro Ile Glu Lys Thr Ile Ser Lys Ala Lys
                        325                 330                 335

Gly Gln Pro Arg Glu Pro Gln Val Tyr Thr Leu Pro Pro Ser Arg Glu
                    340                 345                 350

Glu Met Thr Lys Asn Gln Val Ser Leu Thr Cys Leu Val Lys Gly Phe
                355                 360                 365

Tyr Pro Ser Asp Ile Ala Val Glu Trp Glu Ser Asn Gly Gln Pro Glu
                370                 375                 380

Asn Asn Tyr Lys Thr Thr Pro Pro Val Leu Asp Ser Asp Gly Ser Phe
        385                 390                 395                 400

Phe Leu Tyr Ser Lys Leu Thr Val Asp Lys Ser Arg Trp Gln Gln Gly
                        405                 410                 415

Asn Val Phe Ser Cys Ser Val Met His Glu Ala Leu His Asn His Tyr
                    420                 425                 430

Thr Gln Lys Ser Leu Ser Leu Ser Pro Gly Lys
                435                 440

<210> SEQ ID NO 40
<211> LENGTH: 214
<212> TYPE: PRT
<213> ORGANISM: Artificial Sequence
<220> FEATURE:
<221> NAME/KEY: DOMAIN
<222> LOCATION: (1)..(214)
<223> OTHER INFORMATION: Light chain of antibody 4B5

<400> SEQUENCE: 40

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Gly Val Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Val Ala Thr Tyr Tyr Cys Gln Gln Gly Asn Thr Leu Pro Trp
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160
```

```
Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 41
<211> LENGTH: 447
<212> TYPE: PRT
<213> ORGANISM: Artificial Sequence
<220> FEATURE:
<221> NAME/KEY: CHAIN
<222> LOCATION: (1)..(447)
<223> OTHER INFORMATION: Heavy chain of control antibody GPX4

<400> SEQUENCE: 41

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
        35                  40                  45

Gly Asp Met Tyr Pro Asp Asn Gly Asp Ser Ser Tyr Asn Gln Lys Phe
    50                  55                  60

Arg Glu Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285
```

```
Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 42
<211> LENGTH: 214
<212> TYPE: PRT
<213> ORGANISM: Artificial Sequence
<220> FEATURE:
<221> NAME/KEY: CHAIN
<222> LOCATION: (1)..(214)
<223> OTHER INFORMATION: Light chain of control antibody GPX4

<400> SEQUENCE: 42

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Arg Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
```

```
            195                 200                 205
Phe Asn Arg Gly Glu Cys
    210
```

ANTI-OX40 ANTIBODY, ANTIGEN-BINDING FRAGMENT THEREOF, AND THE PHARMACEUTICAL USE

CROSS-REFERENCE TO RELATED APPLICATIONS

This application is a U.S. National Phase of International PCT Application No. PCT/CN2019/107787 filed Sep. 25, 2019, which claims priority to Chinese Patent Application Serial No. 201811128669.3 filed on Sep. 26, 2018 and Chinese Patent Application Serial No. 201811417666.1 filed on Nov. 26, 2018, the contents of each application are incorporated herein by reference in their entirety.

SEQUENCE LISTING

This application incorporates by reference the material in the ASCII text file titled English_Translation_of_Sequence-_Listing.txt, which was created on Mar. 4, 2021 and is 46.1 KB.

FIELD OF THE INVENTION

The present invention belongs to the field of biomedicine and relates to an anti-OX40 antibody, antigen-binding fragment thereof, a chimeric antibody, a humanized antibody comprising the CDR regions of the anti-OX40 antibody, and a pharmaceutical composition comprising the anti-OX40 antibody and antigen-binding fragment thereof, and the use of the same as an anti-cancer agent.

BACKGROUND OF THE INVENTION

Cancer is a severe health challenge faced by human society for a long time. For solid tumors that have spread, traditional surgery, chemotherapy, and radiotherapy usually exhibit limited effect.

Tumor immunotherapy is continuously a hot spot in the field of tumor therapy. Recent studies have proved that enhancing the function of anti-tumor T cells can be used to counteract cancer. There is a lot of evidence showing that tumor cells "escape" from the immune system by inducing active immune tolerance mediated mainly by regulatory T lymphocytes (Treg; Quezda et al. Immunol Rev 2011; 241:104-118). Therefore, the balance between effector T lymphocytes (Teff) and tolerogenic Treg is essential for effective anti-tumor immunotherapy. Therefore, an effective anti-tumor immune response can be obtained by enhancing the effector function of tumor-specific Teff and/or by reducing the inhibitory function of tumor-specific Treg.

The CD134 (OX40) receptor has been shown to be a key receptor that mediates these responses (Sugamura, K, Ishii, N, Weinberg, A. Therapeutic targeting of the effector T-cell co-stimulatory molecule OX40. Nature Rev Imm 2004; 4:420-431).

OX40 is a member of the tumor necrosis factor receptor (TNFR) superfamily, and is a glycoprotein with a molecular weight of about 50 kDa expressed on the cell surface. The extracellular ligand-binding domain of OX40 consists of 4 cysteine-rich domains (CRD). The natural ligand of OX40 is OX40L (CD252), OX40 and OX40L form an OX40-OX40L complex.

OX40 is mainly expressed on activated T cells, and OX40 is a secondary costimulatory molecule that is expressed 24 to 72 hours after activation. OX40L, a ligand of OX40, is mainly expressed on activated antigen-presenting cells. T lymphocytes expressing OX40 have been confirmed to exist in the draining lymph nodes of patients with various human malignant tumors and cancers. In a mouse model of severe combined immunodeficiency (SCID), the interaction of OX40 and OX40L binding domains can enhance anti-tumor immunity, resulting in tumor growth inhibition of various human malignant tumor cell lines, such as lymphoma, prostate cancer, colon cancer and breast cancer.

Currently, many international pharmaceutical companies are developing monoclonal antibodies against OX40. OX40 antibodies activate immunity through specific stimulation, improve the patient's own immune system response to tumors, and achieve the purpose of killing tumor cells. Related patents are such as WO2013038191, WO2015153513, WO2016179517, WO2017096182, CN110078825A, WO2016196228 and so on. So far, the anti-OX40 antibodies developed by companies such as AstraZeneca and BMS have been in phase II clinical trials, and related products from companies such as Genentech and GSK were also in clinical trials.

However, there is still a need for improvement of the above medicaments in terms of therapeutic effects. Therefore, it is necessary to further develop anti-OX40 antibodies with high selectivity, high affinity and favorable efficacy.

SUMMARY OF THE INVENTION

The present disclosure provides an anti-OX40 antibody or antigen-binding fragment thereof, which specifically binds to human OX40, and comprises the CDRs shown below:
  (i) heavy chain HCDR1, HCDR2 and HCDR3 as shown in SEQ ID NO: 3, 4 and 5 respectively; or HCDR variants having 3, 2 or 1 amino acid difference(s) when compared with HCDR1, HCDR2 and HCDR3 as shown in SEQ ID NO: 3, 4 and 5 respectively; and/or
  light chain LCDR1, LCDR2 and LCDR3 as shown in SEQ ID NO: 6, 7 and 8 respectively; or LCDR variants having 3, 2 or 1 amino acid difference(s) when compared with LCDR1, LCDR2 and LCDR3 as shown in SEQ ID NO: 6, 7 and 8 respectively;
  in particular, heavy chain HCDR1, HCDR2 and HCDR3 as shown in SEQ ID NO: 3, 4 and 5 respectively, and light chain LCDR1, LCDR2 and LCDR3 as shown in SEQ ID NO: 6, 7 and 8 respectively; or
  (ii) heavy chain HCDR1, HCDR2 and HCDR3 as shown in SEQ ID NO: 11, 12 and 13 respectively; or HCDR variants having 3, 2 or 1 amino acid difference(s) when compared with HCDR1, HCDR2 and HCDR3 as shown in SEQ ID NO: 11, 12 and 13 respectively; and/or
  light chain LCDR1, LCDR2 and LCDR3 as shown in SEQ ID NO: 14, 15 and 16 respectively; or LCDR variants having 3, 2 or 1 amino acid difference(s) when compared with LCDR1, LCDR2 and LCDR3 as shown in SEQ ID NO: 14, 15 and 16 respectively;
  in particular, heavy chain HCDR1, HCDR2 and HCDR3 as shown in SEQ ID NO: 11, 12 and 13 respectively, and light chain LCDR1, LCDR2 and LCDR3 as shown in SEQ ID NO: 14, 15 and 16 respectively; or
  (iii) heavy chain HCDR1, HCDR2 and HCDR3 as shown in SEQ ID NO: 11, 33 and 13 respectively; or HCDR variants having 3, 2 or 1 amino acid difference(s) when compared with HCDR1, HCDR2 and HCDR3 as shown in SEQ ID NO: 11, 33 and 13 respectively; and/or
  light chain LCDR1, LCDR2 and LCDR3 as shown in SEQ ID NO: 14, 15 and 16 respectively; or LCDR variants having 3, 2 or 1 amino acid difference(s) when compared with LCDR1, LCDR2 and LCDR3 as shown in SEQ ID NO: 14, 15 and 16 respectively;
in particular, heavy chain HCDR1, HCDR2 and HCDR3 as shown in SEQ ID NO: 11, 33 and 13 respectively, and light chain LCDR1, LCDR2 and LCDR3 as shown in SEQ ID NO: 14, 15 and 16 respectively; or
(iv) heavy chain HCDR1, HCDR2 and HCDR3 as shown in SEQ ID NO: 11, 34 and 13 respectively; or HCDR variants having 3, 2 or 1 amino acid difference(s) when compared with HCDR1, HCDR2 and HCDR3 as shown in SEQ ID NO: 11, 34 and 13 respectively; and/or
light chain LCDR1, LCDR2 and LCDR3 as shown in SEQ ID NO: 14, 15 and 16 respectively; or LCDR variants having 3, 2 or 1 amino acid difference(s) when compared with LCDR1, LCDR2 and LCDR3 as shown in SEQ ID NO: 14, 15 and 16 respectively;
in particular, heavy chain HCDR1, HCDR2 and HCDR3 as shown in SEQ ID NO: 11, 34 and 13 respectively, and light chain LCDR1, LCDR2 and LCDR3 as shown in SEQ ID NO: 14, 15 and 16 respectively.

In some embodiments, the anti-OX40 antibody or antigen-binding fragment thereof is a murine antibody, chimeric antibody, humanized antibody, human antibody or fragment thereof; in particular, a humanized antibody.

In some embodiments, the CDRs (comprising 3 heavy chain CDRs and 3 light chain CDRs) of the monoclonal antibody or antigen-binding fragment are allowed to comprise 3, 2 or 1 amino acid difference(s) (i.e., CDR variants). The CDR variants are obtained by affinity maturation method.

In some embodiments, the affinity (KD) of the monoclonal antibody or antigen-binding fragment to OX40 is less than $10^{-8}$M, less than $10^{-9}$M, or less than $10^{1o}$ M.

In some embodiments, the murine antibody comprises a heavy chain variable region and a light chain variable region as shown below:
(i) the amino acid sequence of the heavy chain variable region is as shown in SEQ ID NO:1; or has at least 70%, at least 75%, at least 80%, at least 85%, at least 90%, at least 91%, at least 92%, at least 93%, at least 94%, at least 95%, at least 96%, at least 97%, at least 98% or at least 99% sequence identity to SEQ ID NO:1; and/or
the amino acid sequence of the light chain variable region is as shown in SEQ ID NO:2; or has at least 70%, at least 75%, at least 80%, at least 85%, at least 90%, at least 91%, at least 92%, at least 93%, at least 94%, at least 95%, at least 96%, at least 97%, at least 98% or at least 99% sequence identity to SEQ ID NO:2;
(ii) the amino acid sequence of the heavy chain variable region is as shown in SEQ ID NO:9; or has at least 70%, at least 75%, at least 80%, at least 85%, at least 90%, at least 91%, at least 92%, at least 93%, at least 94%, at least 95%, at least 96%, at least 97%, at least 98% or at least 99% sequence identity to SEQ ID NO:9; and/or
the amino acid sequence of the light chain variable region is as shown in SEQ ID NO:10; or has at least 70%, at least 75%, at least 80%, at least 85%, at least 90%, at least 91%, at least 92%, at least 93%, at least 94%, at least 95%, at least 96%, at least 97%, at least 98% or at least 99% sequence identity to SEQ ID NO:10.

In some embodiments, the humanized antibody comprises FR region(s) derived from human germline or mutant sequence(s) thereof.

In some embodiments, wherein the humanized antibody comprises any one of:
(i) a heavy chain variable region, which is as shown in any one of SEQ ID NO: 17, 18, 31 or 32; or has at least 70%, at least 75%, at least 80%, at least 85%, at least 90%, at least 91%, at least 92%, at least 93%, at least 94%, at least 95%, at least 96%, at least 97%, at least 98% or at least 99% sequence identity to SEQ ID NO: 17, 18, 31 or 32; or
(ii) a heavy chain variable region, which is as shown in any one of SEQ ID NO: 26, 27, 28, 29 or 30; or has at least 70%, at least 75%, at least 80%, at least 85%, at least 90%, at least 91%, at least 92%, at least 93%, at least 94%, at least 95%, at least 96%, at least 97%, at least 98% or at least 99% sequence identity to SEQ ID NO: 26, 27, 28, 29 or 30.

In one embodiment, the anti-OX40 antibody or antigen-binding fragment thereof comprises:
(i) a light chain variable region, which is as shown in SEQ ID NO: 19 or 20; or has at least 70%, at least 75%, at least 80%, at least 85%, at least 90%, at least 91%, at least 92%, at least 93%, at least 94%, at least 95%, at least 96%, at least 97%, at least 98% or at least 99% sequence identity to SEQ ID NO: 19 or 20; or
(ii) a light chain variable region, which is as shown in any one of SEQ ID NO: 21, 22, 23, 24 or 25; or has at least 70%, at least 75%, at least 80%, at least 85%, at least 90%, at least 91%, at least 92%, at least 93%, at least 94%, at least 95%, at least 96%, at least 97%, at least 98% or at least 99% sequence identity to SEQ ID NO: 21, 22, 23, 24 or 25.

In some particular embodiments, the anti-OX40 antibody or antigen-binding fragment thereof comprises:
(i) a heavy chain variable region as shown in any one of SEQ ID NO: 17, 18, 31 and 32 and a light chain variable region as shown in SEQ ID NO: 19 or 20; or
(ii) a heavy chain variable region as shown in any one of SEQ ID NO: 26, 27, 28, 29 and 30 and a light chain variable region as shown in any one of SEQ ID NO: 21, 22, 23, 24 and 25.

In some particular embodiments, the anti-OX40 antibody or antigen-binding fragment thereof comprises variable regions as shown below:
(1) a heavy chain variable region as shown in SEQ ID NO: 17, and a light chain variable region as shown in SEQ ID NO: 19;
(2) a heavy chain variable region as shown in SEQ ID NO: 18, and a light chain variable region as shown in SEQ ID NO: 19;
(3) a heavy chain variable region as shown in SEQ ID NO: 31, and a light chain variable region as shown in SEQ ID NO: 19;
(4) a heavy chain variable region as shown in SEQ ID NO: 32, and a light chain variable region as shown in SEQ ID NO: 19;
(5) a heavy chain variable region as shown in SEQ ID NO: 17, and a light chain variable region as shown in SEQ ID NO: 20;
(6) a heavy chain variable region as shown in SEQ ID NO: 18, and a light chain variable region as shown in SEQ ID NO: 20;
(7) a heavy chain variable region as shown in SEQ ID NO: 31, and a light chain variable region as shown in SEQ ID NO: 20; or
(8) a heavy chain variable region as shown in SEQ ID NO: 32, and a light chain variable region as shown in SEQ ID NO: 20.

In some embodiments, the anti-OX40 antibody or antigen-binding fragment thereof comprises variable regions as shown below:
(1) a heavy chain variable region as shown in SEQ ID NO: 26, and a light chain variable region as shown in SEQ ID NO: 21;
(2) a heavy chain variable region as shown in SEQ ID NO: 26, and a light chain variable region as shown in SEQ ID NO: 22;
(3) a heavy chain variable region as shown in SEQ ID NO: 26, and a light chain variable region as shown in SEQ ID NO: 23;
(4) a heavy chain variable region as shown in SEQ ID NO: 26, and a light chain variable region as shown in SEQ ID NO: 24;
(5) a heavy chain variable region as shown in SEQ ID NO: 26, and a light chain variable region as shown in SEQ ID NO: 25;
(6) a heavy chain variable region as shown in SEQ ID NO: 27, and a light chain variable region as shown in SEQ ID NO: 21;
(7) a heavy chain variable region as shown in SEQ ID NO: 27, and a light chain variable region as shown in SEQ ID NO: 22;
(8) a heavy chain variable region as shown in SEQ ID NO: 27, and a light chain variable region as shown in SEQ ID NO: 23;
(9) a heavy chain variable region as shown in SEQ ID NO: 27, and a light chain variable region as shown in SEQ ID NO: 24;
(10) a heavy chain variable region as shown in SEQ ID NO: 27, and a light chain variable region as shown in SEQ ID NO: 25;
(11) a heavy chain variable region as shown in SEQ ID NO: 28, and a light chain variable region as shown in SEQ ID NO: 21;
(12) a heavy chain variable region as shown in SEQ ID NO: 28, and a light chain variable region as shown in SEQ ID NO: 22;
(13) a heavy chain variable region as shown in SEQ ID NO: 28, and a light chain variable region as shown in SEQ ID NO: 23;
(14) a heavy chain variable region as shown in SEQ ID NO: 28, and a light chain variable region as shown in SEQ ID NO: 24;
(15) a heavy chain variable region as shown in SEQ ID NO: 28, and a light chain variable region as shown in SEQ ID NO: 25;
(16) a heavy chain variable region as shown in SEQ ID NO: 29, and a light chain variable region as shown in SEQ ID NO: 21;
(17) a heavy chain variable region as shown in SEQ ID NO: 29, and a light chain variable region as shown in SEQ ID NO: 22;
(18) a heavy chain variable region as shown in SEQ ID NO: 29, and a light chain variable region as shown in SEQ ID NO: 23;
(19) a heavy chain variable region as shown in SEQ ID NO: 29, and a light chain variable region as shown in SEQ ID NO: 24;
(20) a heavy chain variable region as shown in SEQ ID NO: 29, and a light chain variable region as shown in SEQ ID NO: 25;
(21) a heavy chain variable region as shown in SEQ ID NO: 30, and a light chain variable region as shown in SEQ ID NO: 21;
(22) a heavy chain variable region as shown in SEQ ID NO: 30, and a light chain variable region as shown in SEQ ID NO: 22;
(23) a heavy chain variable region as shown in SEQ ID NO: 30, and a light chain variable region as shown in SEQ ID NO: 23;
(24) a heavy chain variable region as shown in SEQ ID NO: 30, and a light chain variable region as shown in SEQ ID NO: 24; and
(25) a heavy chain variable region as shown in SEQ ID NO: 30, and a light chain variable region as shown in SEQ ID NO: 25.

In some embodiments, the anti-OX40 antibody comprises a constant region; in some particular embodiments, the antibody is a chimeric antibody or a humanized antibody, and the heavy chain constant region of the antibody is derived from human IgG1, IgG2, IgG3, or IgG4 or the mutant sequence(s) thereof, the light chain constant region is derived from human kappa, lambda chain or the mutant sequence(s) thereof; in other particular embodiments, the amino acid sequence of the heavy chain constant region is as shown in SEQ ID NO: 35 or has at least 70%, at least 75%, at least 80%, at least 85%, at least 90%, at least 91%, at least 92%, at least 93%, at least 94%, at least 95%, at least 96%, at least 97%, at least 98% or at least 99% sequence identity to SEQ ID NO: 35; the amino acid sequence of the light chain constant region is as shown in SEQ ID NO: 36 or has at least 70%, at least 75%, at least 80%, at least 85%, at least 90%, at least 91%, at least 92%, at least 93%, at least 94%, at least 95%, at least 96%, at least 97%, at least 98% or at least 99% sequence identity to SEQ ID NO: 36.

In some embodiments, the heavy chain amino acid sequence of the anti-OX40 antibody is as shown in SEQ ID NO: 39 or 37 or has at least 70%, at least 75%, at least 80%, at least 85%, at least 90%, at least 91%, at least 92%, at least 93%, at least 94%, at least 95%, at least 96%, at least 97%, at least 98% or at least 99% sequence identity to SEQ ID NO: 39 or 37, and/or, the light chain amino acid sequence of the anti-OX40 is as shown in SEQ ID NO: 40 or 38 or has at least 70%, at least 75%, at least 80%, at least 85%, at least 90%, at least 91%, at least 92%, at least 93%, at least 94%, at least 95%, at least 96%, at least 97%, at least 98% or at least 99% sequence identity to SEQ ID NO: 40 or 38.

In one embodiment, the anti-OX40 antibody comprises:
(i) a heavy chain, the amino acid sequence of which is as shown in SEQ ID NO: 37 or has at least 85% sequence identity to SEQ ID NO: 37, and
a light chain, the amino acid sequence of which is as shown in SEQ ID NO: 38 or has at least 85% sequence identity to SEQ ID NO: 38; or
(ii) a heavy chain, the amino acid sequence of which is as shown in SEQ ID NO: 39 or has at least 85% sequence identity to SEQ ID NO: 39, and
a light chain, the amino acid sequence of which is as shown in SEQ ID NO: 40 or has at least 85% sequence identity to SEQ ID NO: 40.

The present disclosure also provides an anti-OX40 antibody or antigen-binding fragment thereof, the anti-OX40 antibody or antigen-binding fragment thereof competes with any antibody or antigen-binding fragment thereof described above for the binding to human OX40, or competes with any antibody or antigen-binding fragment thereof described above for binding to the same OX40 epitope.

The present disclosure also provides a pharmaceutical composition, which comprises:

a therapeutically/preventively effective amount of the anti-OX40 antibody or antigen-binding fragment thereof described above, and one or more pharmaceutically acceptable carriers, diluents, buffers or excipients.

In some particular embodiments, the pharmaceutical composition may be prepared in a unit dose form, and the unit dose may comprise 0.01 to 99% by weight of the anti-OX40 antibody or antigen-binding fragment thereof; or the amount of the monoclonal antibody or antigen-binding fragment thereof comprised in the pharmaceutical composition is from 0.1 to 2000 mg/unit dose. In some particular embodiments, the amount of the monoclonal antibody or antigen-binding fragment thereof is from 1 to 1000 mg.

In some particular embodiments, the monoclonal antibody or antigen-binding fragment thereof may be the one and only active ingredient comprised in the composition; in other particular embodiments, the monoclonal antibody or antigen-binding fragment thereof is used in combination with other active ingredients.

The present disclosure also provides an isolated nucleic acid molecule, which encodes the anti-OX40 antibody or antigen-binding fragment thereof described above. In the context herein, the complementary sequence of the nucleic acid molecule is also included in the scope of this application.

The present disclosure also provides a vector comprising the nucleic acid molecule described above. The vector can be a eukaryotic expression vector, a prokaryotic expression vector or a viral vector.

The present disclosure also provides a host cell transformed with the vector described above, and the host cell is selected from the group consisting of prokaryotic cells and eukaryotic cells.

In some particular embodiments, the host cell is a eukaryotic cell. In some particular embodiments, the host cell is a mammalian cell, wherein the mammalian cell comprises but not limited to CHO, HEK293, and NSO. It should be understood that the host cell of the present disclosure does not involve any cell capable of developing into humans.

The present disclosure also provides a method for preparing the anti-OX40 antibody or antigen-binding fragment thereof described above, the method comprises:

cultivating the host cell described above;

recovering the antibody or antigen-binding fragment thereof;

optionally, purifying the antibody or antigen-binding fragment thereof.

The present disclosure also provides a method for detecting or measuring human OX40, the method comprises:

contacting the anti-OX40 antibody or antigen-binding fragment thereof as described above with a sample (e.g. from human);

optionally, determining the amount of OX40 in the sample, or determining whether OX40 is present or not.

The present disclosure also provides a reagent for detecting or measuring human OX40, the reagent comprises any one of the anti-OX40 antibodies or antigen-binding fragment thereof described above.

The present disclosure also provides a diagnostic agent for diseases related to human OX40, the diagnostic agent comprises the anti-OX40 antibody or antigen-binding fragment thereof described above.

The present disclosure also provides a method for diagnosing diseases related to human OX40, the method comprises detecting or measuring human OX40 or OX40-positive cells using the anti-OX40 antibody or antigen-binding fragment thereof described above.

The present disclosure also provides the use of the anti-OX40 antibody or antigen-binding fragment thereof in the preparation of a diagnostic agent for diseases related to human OX40.

The present disclosure also provides a method for treating disease or disorder, which comprises administering to a subject an effective amount of the anti-OX40 antibody or antigen-binding fragment thereof, or a pharmaceutical composition comprising the OX40 antibody or fragment thereof described above.

In some embodiments, the disease or disorder may be cancer or cell-proliferative disease. In some particular embodiments, the cancer is lung cancer, prostate cancer, breast cancer, head and neck cancer, esophageal cancer, gastric carcinoma, colon cancer, colorectal cancer, bladder cancer, cervical cancer, uterine cancer, ovarian cancer, liver cancer, melanoma, kidney cancer, squamous cell carcinoma, hematological cancer or any other disease or disorder characterized by uncontrolled cell growth.

In some particular embodiments, the hematological cancer comprises but is not limited to acute and chronic myelogenous leukemia, acute lymphocytic leukemia, chronic lymphocytic leukemia, bone marrow tissue proliferative disease, multiple myeloma, Hodgkin's disease, non-Hodgkin's lymphoma, B-cell lymphoma, T-cell lymphoma, follicular center cell lymphoma and chronic myeloid leukemia.

The present disclosure also provides the use of the anti-OX40 antibody or antigen-binding fragment thereof described above, or the pharmaceutical composition comprising the OX40 antibody or fragment thereof described above, in the preparation of a medicine for enhancing the immune response in a human subject.

The present disclosure also provides the use of the anti-OX40 antibody or antigen-binding fragment thereof described above, or the pharmaceutical composition comprising the OX40 antibody or fragment thereof described above, in the preparation of a medicament for the treatment/prevention of cancer.

The present disclosure also provides the use of the anti-OX40 antibody or antigen-binding fragment thereof described above, or the pharmaceutical composition comprising the OX40 antibody or fragment thereof described above, in the preparation of a kit.

In some embodiments, the enhanced immune response comprises an increase in the immunostimulatory/effector function of T effector cells, and/or a down-regulation of the immunosuppressive function of T regulatory cells. Wherein, the increase may be the result of cell proliferation, and the down-regulation may be the result of absence of increase in cell number (or decrease in cell number).

The present disclosure provides the anti-human OX40 antibody or fragment thereof for use in one or more of the following: inhibiting Treg function (for example, inhibiting the suppressive function of Treg), killing OX40-expressing cells (for example, cells expressing high level of OX40), improving effector T cell function and/or improving memory T cell function, reducing tumor immunity, enhancing T cell function and/or reducing OX40-expressing cells.

The present disclosure provides the use of the anti-OX40 antibody or fragment thereof for the following: treating cancer, stimulating immune response in a subject, stimulating antigen-specific T cell response, activating or co-stimulating T cells, increasing cytokines production in T cells (such as IL-2 and/or IFN-γ), and/or increasing T cell proliferation, reducing or depleting the number of T regulatory cells in tumor, and/or inhibiting the growth of tumor cells.

The present disclosure also provides the use of the anti-OX40 antibody in the preparation of an agent, the agent is for use in stimulating immune response in a subject, stimulating antigen-specific T cell response, activating or co-stimulating T cells, increasing IL-2 and/or IFN-γ production in T cells and/or T cell proliferation, reducing or depleting the number of T regulatory cells in tumor, and/or inhibiting the growth of tumor cells.

DESCRIPTION OF THE DRAWINGS

FIG. 1A shows the result of the affinity of the murine antibody m2G3 and the chimeric antibody ch2G3, with m2G3-NC and ch2G3-NC as negative controls; FIG. 1B shows the result of the affinity of the murine antibody m4B5 and the chimeric antibody ch4B5, with m4B5-NC and ch4B5-NC as negative controls.

FIG. 3A shows the changes in tumor volume in different mice after administration; FIG. 3B shows the effect of different anti-OX40 antibodies on tumor weight in mice after administration. The results show that on day 20 after dosing treatment, when the dose is at 3 mg/kg, the tumor inhibition rate of 2G3 antibody is up to 97%.

TERMINOLOGY

Figure 1A:
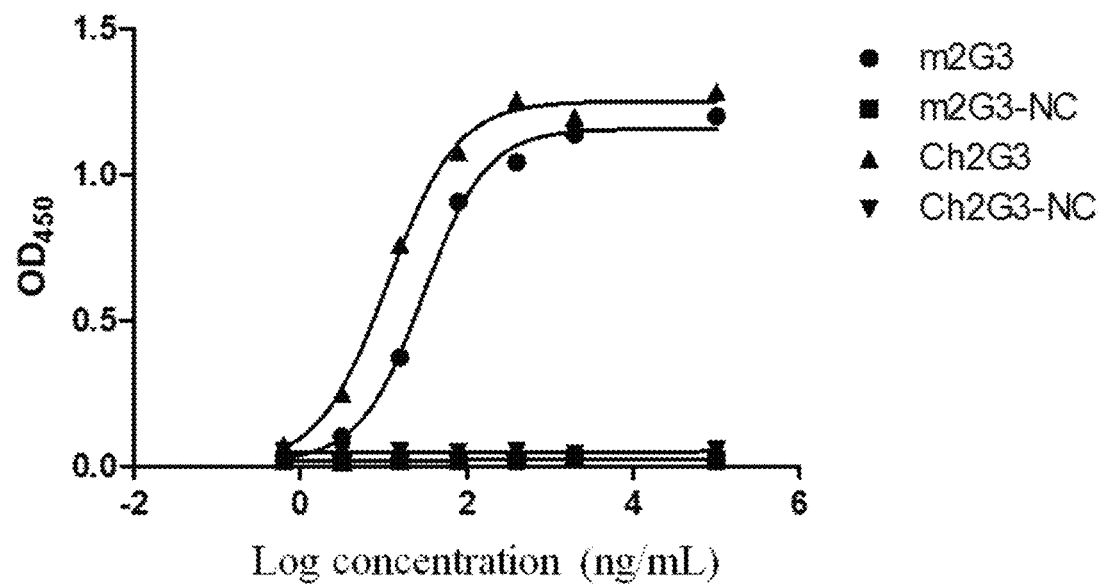
FIG. 1A to FIG. 1B: ELISA test results showing the affinity of murine antibody and chimeric antibody to human OX40.

In order to make the present disclosure being more readily understood, certain technical and scientific terms are specifically defined below. Unless specifically defined elsewhere herein, all other technical and scientific terms used herein have the meaning commonly understood by one of ordinary skill in the art to which present application pertains.

The term "enhancing T cell function" means inducing, causing or stimulating effector or memory T cells, so that they have renewal, sustained or amplified biological functions. Examples of enhanced T cell function include: increased secretion of γ-interferon from $CD8^+$ effector T cells, increased secretion of γ-interferon from $CD4^+$ memory and/or effector T cells, increased proliferation of $CD4^+$ effector and/or the memory T cells, increased proliferation of $CD8^+$ effector T cells, and increased response to antigen (e.g., clearance), when compared with the level before treatment.

The term "enhancing immune response" refers to stimulating, irritating, increasing, improving or enhancing the response of the immune system in mammalian. The immune response can be a cellular response (i.e., cell-mediated, such as cytotoxic T lymphocyte-mediated) or a humoral response (i.e., antibody-mediated response), and can be the primary or secondary immune response. Examples of enhanced immune response include: increased activity of $CD4^+$ helper T cell and production of cytotoxic T cells. The enhanced immune response can be evaluated by some in vitro or in vivo measurements known to those skilled in the art, comprising but not limited to cytotoxic T lymphocyte assay, cytokine release (such as IL-2 production), regression of tumor, and survival of tumor-carrying animals, antibody production, proliferation of immune cells, expression of cell surface marker and cytotoxicity. In one embodiment, the method enhances cellular immune response, particularly cytotoxic T cell response.

"Tumor immunity" refers to the process by which tumors escape from immune recognition and clearance. As a treatment concept, the tumor will be recognized and attacked by the immune system and consequently the patient will be treated, when tumor immunity is weakened in its ability to escape from immune recognition and clearance. Examples of tumor recognition include binding to tumor, shrinkage of tumor, and clearance of tumor.

"T effector cells" ("Teffs") refer to T cells having cytolytic activity (for example, $CD4^+$ and $CD8^+$ T cells) and T helper (Th) cells. Teffs secrete cytokines and activate and guide immune cells other than regulatory T cells (Treg cells). The anti-OX40 antibodies described in the present disclosure can activate Teff cells, such as $CD4^+$ and $CD8^+$ Teff cells.

"Regulatory T cells" or "Treg cells" mean a specialized type of $CD4^+$ T cells that can suppress the response of other T cells. Treg cells are characterized by expressing CD4, α subunit of IL-2 receptor (CD25), and the transcription factor forkhead box P3 (FOXP3) (Sakaguchi, Annu Rev Immunol 22, 531-62 (2004)), and play a vital role in the induction and maintenance of peripheral autologous tolerance. The tolerance targets against antigens expressed by tumors.

"OX40" refers to a receptor that binds to OX40 ligand (OX40-L), and it is a member of the TNF-receptor superfamily. OX40 is also known as tumor necrosis factor receptor superfamily member 4 (TNFRSF4), ACT35, IMD16, TXGP1L and CD134. The term "OX40" includes any variant or isotype of OX40 that is naturally expressed by a cell. Therefore, the OX40 antibodies or fragment thereof described in the present disclosure can cross-react with OX40 from species other than humans (for example, cynomolgus monkey OX40). Alternatively, the OX40 antibodies or fragment thereof may be specific for human OX40, and does not exhibit cross-reactivity with OX40 of other species.

OX40 or variant and isoform thereof is isolated from cells or tissues in which it is naturally expressed, or recombinantly produced using techniques well known in the art and/or in the present disclosure. Unless otherwise specified, "OX40" can be natural OX40 derived from any vertebrate source, comprising mammals such as primates (e.g., humans) and rodents (e.g., mice and rats). The term covers "full length", unprocessed OX40 and any forms of OX40 due to processing occurred within a cell. The term also covers naturally occurring variants of OX40, such as splicing variants or allelic variants.

"OX40 activation" refers to the activation of the OX40 receptor. Generally, OX40 activation leads to signaling.

An "anti-OX40 antibody" or "an antibody that binds to OX40" refers to an antibody that can bind to OX40 with sufficient affinity so that the antibody can be used as a diagnostic and/or therapeutic agent for targeting OX40.

The term "reducing OX40-expressing cells" means that the anti-OX40 antibody or fragment thereof kills or eliminates OX40-expressing cells. Reducing OX40-expressing cells can be achieved through various mechanisms, such as antibody-dependent cell mediated cytotoxicity (ADCC) and/or phagocytosis.

The term "cytokine" is a general term for a type of proteins that are released by a population of cells, and the cytokines act as intercellular mediators effecting on another cell. Examples of such cytokines are lymphokines, monocytes; interleukins (ILs), such as IL-1, IL-1α, IL-2, IL-3, IL-4, IL-5, IL-6, IL-7, IL-8, IL-9, IL-11, IL-12, IL-15; tumor necrosis factors, such as TNF-α or TNF-β; and other polypeptide factors, comprising LIF and kit ligand (KL) and γ-Interferon. As used in the present disclosure, the term cytokines involve proteins from natural sources or from recombinant cell culture, and the biologically active equivalents thereof, comprising small molecular entities produced by artificial synthesis, and pharmaceutically acceptable derivatives and salts thereof.

As used in the present disclosure, the three-letter code and the single-letter code for amino acids are as described in J. Biol. Chem, 243, p3558 (1968).

The term "antibody" is not limited by any specific method for producing antibodies. For example, it involves recombinant antibodies, monoclonal antibodies, and polyclonal antibodies. The antibodies may be antibodies of different isotypes, for example, IgG (e.g., IgG1, IgG2, IgG3 or IgG4 subtype), IgA1, IgA2, IgD, IgE or IgM antibodies.

Near the N-terminus of the antibody heavy chain and light chain, a sequence of about 110 amino acid varies largely, known as variable region (V region); the rest of the amino acid sequence near the C-terminus is relative stable, known as constant region (C region). The variable region comprises three hypervariable regions (HVRs) and four framework regions (FRs) having relatively conserved sequence. The three hypervariable regions determine the specificity of the antibody, also known as complementarity determining regions (CDRs). Each light chain variable region (VL) and each heavy chain variable region (VH) is composed of three CDRs and four FRs, with an order from the amino terminus to the carboxyl terminus being: FR1, CDR1, FR2, CDR2, FR3, CDR3, and FR4. Three light chain CDRs refer to LCDR1, LCDR2, and LCDR3; three heavy chain CDRs refer to HCDR1, HCDR2 and HCDR3.

The number and position of the CDR amino acid residues in the LCVR region and HCVR region of the antibody or antigen-binding fragment thereof described in the present disclosure comply with the known Kabat numbering criteria (for LCDR1-3, HCDR1-3).

The term "recombinant human antibody" includes human antibodies prepared, expressed, created or isolated by recombinant method, and the techniques and methods involved are well known in the art, such as:
(1) antibodies isolated from human immunoglobulin gene transgenic animals or trans-chromosomal animals (e.g., mice), or hybridoma prepared therefrom;
(2) antibodies isolated from transformed host cells that express the antibodies, such as transfectoma;
(3) antibodies isolated from a combinatorial library of recombinant human antibody; and
(4) antibodies prepared, expressed, created or isolated by splicing human immunoglobulin gene sequence to another DNA sequences, or the like. Such recombinant human antibodies comprise variable regions and constant regions, which involve specific human germline immunoglobulin sequences encoded by germline genes, but also involve subsequent rearrangements and mutations, such as those occured during the antibody maturation.

The antibodies of the present disclosure refer to murine antibodies, chimeric antibodies, humanized antibodies, and human antibodies.

In some embodiments, the antibodies are humanized antibodies.

The term "murine antibody" herein refers to monoclonal antibodies against human OX40, which are prepared according to the knowledge and skills in the art. During the preparation, a test object is injected with OX40 antigen, and then splenocytes (B lymphocytes) expressing the antibody which possesses desired sequence or functional characteristics are separated, and then the B lymphocytes are fused with myeloma cells to obtain corresponding hybridoma cells.

In some particular embodiments, the murine OX40 antibody or antigen-binding fragment thereof further comprises light chain constant region(s) of murine κ, λ chain or variant(s) thereof, or further comprises heavy chain constant region(s) of murine IgG1, IgG2, IgG3 or IgG4, or variant(s) thereof.

The term "human antibody" includes antibodies having variable and constant region(s) from human germline immunoglobulin sequences. Human antibodies of the present disclosure may include amino acid residues that are not encoded by human germline immunoglobulin sequences (e.g., mutations introduced by random or site-specific mutagenesis in vitro or by somatic mutation in vivo). However, the term "human antibody" does not refer to such an antibody in which CDR sequences derived from other mammalian species (such as mouse) germline have been grafted onto human framework sequence (i.e., "humanized antibody").

The term "humanized antibody" refers to antibodies generated by grafting non-human species CDR sequences onto variable region framework of human antibody; that is, antibodies produced from different types of human germline antibody framework sequences. Humanized antibodies overcome the heterogenous response induced by chimeric antibodies which carry a large amount of heterogeneous protein components. Such framework sequences can be obtained from public DNA databases or published references that include germline antibody gene sequences. For example, the germline DNA sequences of human heavy chain and light chain variable region genes can be obtained in "VBase" human germline sequence database (www.mrccpe.com.ac.uk/vbase), and also in Kabat, E. A, et al., 1991 Sequences of Proteins of Immunological Interest, 5th edition. To avoid a decrease of activity along with the decrease of immunogenicity, the FR sequences in variable region of the human antibody would be subjected to minimum back mutation or reverse mutation to maintain the activity. The humanized antibodies of the present disclosure also include humanized antibodies that are obtained after further affinity maturation of CDRs by phage display or yeast display.

In the case of CDR grafting, the reduced affinity of the resulting OX40 antibody (or antigen-binding fragment thereof) to the antigen is due to changes occurred in the framework residues which are responsible for the contact with the antigen. Such interaction can be the result of hypermutation in somatic cells. Therefore, there is still a need to graft such donor framework amino acids onto the framework of humanized antibodies. The amino acid residues from non-human OX40 antibody or antigen-binding fragment thereof involved in antigen-binding can be identified by detecting the sequence and structure of the variable region of non-human monoclonal antibody. Residues in a CDR donor framework that are different from those in the germline can be considered to be related. Where the closest germline cannot be determined, the sequence can be aligned against the consensus sequence of a subtype or against the consensus sequence of a murine sequence with high percentage of similarity. Rare framework residues are thought to be the result of hypermutation in somatic cells and thus play an important role in binding. In some embodiments of the present disclosure, the antibody light chain of the OX40 humanized antibody further comprises a light chain constant region of a human kappa, lambda chain or the variant thereof. The antibody heavy chain of the OX40 humanized antibody further comprises a heavy chain constant region of human IgG1, IgG2, IgG3, IgG4 or the variant thereof; in particular, a human IgG1 heavy chain constant region.

The term "back mutation" refers to reversion of the amino acid mutation(s) in the FR region of a human antibody to the amino acid residue(s) at the corresponding position(s) of the original antibody source. Usually, to avoid the decrease in immunogenicity caused by a humanized antibody which in turn leads to the decrease in activity, the variable region of the humanized antibody can be subjected to minimal back mutation(s) to maintain the activity of the antibody.

The term "chimeric antibody", is an antibody which is formed by fusing the variable region of a non-human antibody with the constant region of a human antibody, the chimeric antibody can alleviate the immune response induced by non-human antibody. As an example, to establish a chimeric antibody, hybridoma secreting specific murine monoclonal antibody shall be established firstly, a variable region gene is then cloned from mouse hybridomas, then a constant region gene of a human antibody is cloned as desired, the mouse variable region gene is ligated to the human constant region gene to form a chimeric gene which can be inserted into a human vector, and finally the chimeric antibody molecule is expressed in an eukaryotic or prokaryotic industrial system. The constant region of a human antibody is selected from heavy chain constant region(s) of human IgG1, IgG2, IgG3 or IgG4 or variant(s) thereof. In particular, a chimeric antibody comprises human IgG1 heavy chain constant region(s).

The term "antigen-binding fragment" or "functional fragment" of an antibody refers to one or more fragments of the antibody that retain the ability to specifically bind to an antigen (e.g., OX40). It has been shown that fragments of a full-length antibody can be used to achieve function of antigen-binding. Examples of the binding fragments contained in the term "antigen-binding fragment" of an antibody involve:

(i) Fab fragment, a monovalent fragment consisting of VL, VH, CL and CH1 domains;
(ii) F(ab')$_2$ fragment, a bivalent fragment formed by two Fab fragments connected by disulfide bridge(s) in the hinge region;
(iii) Fd fragment consisting of VH and CH1 domains;
(iv) Fv fragment consisting of the VH and VL domains from one arm of the antibody;
(v) single domain or dAb fragment (Ward et al., (1989) Nature, 341:544-546), which consists of a VH domain; and
(vi) isolated complementarity determining region (CDR); or
(vii) optionally, a combination of two or more isolated CDRs connected by a synthetic linker.

In addition, the VL domain and VH domain of the Fv fragment are encoded by two separate genes, however they can be linked by a synthetic linker by using recombinant methods, to generate a single protein chain in which a monovalent molecular is formed by pairing the VL with VH domain (referred to as single chain Fv (scFv); see, e.g., Bird et al. (1988): Science 242:423-426; and Huston et al (1988) Proc. Natl. Acad. Sci USA 85:5879-5883). Such single chain antibodies are also intended to be included in the term "antigen binding fragment" of an antibody. Such antibody fragments are obtained using conventional techniques known by the skilled persons in the art, and can be screened for functional fragments by using the same method as that for an intact antibody. Antigen binding portions can be produced by recombinant DNA technology or by enzymatic or chemical digestion of an intact immunoglobulin. Antibodies can be in the forms of different isotypes, e.g., IgG (e.g., IgG1, IgG2, IgG3 or IgG4 subtype), IgA1, IgA2, IgD, IgE or IgM antibody.

In some embodiments, "antigen-binding fragment" refers to Fab, Fv, sFv, F(ab')2, linear antibody, single-chain antibody, scFv, sdAb, sdFv, nanobody, peptibody, domain antibody and multispecific antibody (bispecific antibody, diabody, triabody and tetrabody, tandem di-scFv, tandem tri-scFv) having antigen-binding activity.

Fab is an antibody fragment obtained by treating an IgG antibody molecule with a papain (which cleaves the amino acid residue at position 224 in H chain). The obtained fragment has a molecular weight of about 50,000 and antigen-binding activity, in which almost half of H chain to the N-terminus and the entire L chain are bound together through a disulfide bond. The Fab in the present disclosure can be produced by treating the monoclonal antibody of the present disclosure (which specifically recognizes human OX40 and binds to the amino acid sequence of extracellular domain or the 3D structure thereof) with papain. Further, the Fab can be produced by inserting DNA encoding Fab of the antibody into a prokaryotic expression vector or eukaryotic expression vector and introducing the vector into a prokaryote or eukaryote to express the Fab.

"F(ab')2" refers to an antibody fragment having a molecular weight of about 100,000 and antigen-binding activity, which is obtained by digesting the part downstream of the two disulfide bonds in the hinge region of IgG by pepsin. F(ab')2 contains two Fabs connected at the hinge region.

F(ab')2 of the present disclosure can be produced by treating the monoclonal antibody of the present disclosure with pepsin. Also, F(ab')2 can be produced by connecting the Fab' described below via thioether bond or disulfide bond.

Fab' is an antibody fragment having a molecular weight of about 50,000 and having antigen-binding activity, which is obtained by cleaving the disulfide bond at the hinge region of the above-mentioned F(ab')2. The Fab' of the present disclosure can be produced by treating F(ab')2 of the present disclosure with a reducing agent such as dithiothreitol.

Further, the Fab' can be produced by inserting DNA encoding Fab' of the antibody into a prokaryotic expression vector or eukaryotic expression vector and introducing the vector into a prokaryote or eukaryote to express the Fab'.

The term "single chain antibody", "single chain Fv" or "scFv" refers to a molecule comprising antibody heavy chain variable domain (or region; VH) connected to antibody light chain variable domain (or region; VL) by a linker. Such scFv molecules have general structure of NH$_2$-VL-linker-VH-COOH or NH$_2$-VH-linker-VL-COOH. A suitable linker in the prior art consists of repeated GGGGS amino acid sequence or variant thereof, for example, variant with 1-4 repeats (Holliger et al. (1993), Proc. Natl. Acad. Sci. USA 90:6444-6448). Other linkers that can be used in the present disclosure are described by Alfthan et al. (1995), Protein Eng. 8:725-731, Choi et al. (2001), Eur. J. Immunol. 31:94-106, Hu et al. (1996), Cancer Res. 56:3055-3061, Kipriyanov et al. (1999), J. Mol. Biol. 293:41-56 and Roovers et al. (2001), Cancer Immunol.

The scFv of the present disclosure can be produced by the following steps: obtaining cDNAs encoding the VH and VL of the monoclonal antibody of the present disclosure, constructing a DNA encoding the scFv, inserting the DNA into a prokaryotic or eukaryotic expression vector, and then introducing the expression vector into a prokaryote or eukaryote to express the scFv.

"Diabody" is an antibody fragment in which the scFv is dimerized, and it is an antibody fragment having divalent antigen-binding activity. In the divalent antigen-binding activity, the two antigens may be the same or different.

The diabody of the present disclosure can be produced by the following steps: obtaining cDNAs encoding VH and VL of the monoclonal antibody of the present disclosure, constructing a DNA encoding scFv to make the length of a linker peptide being of 8 or less amino acid residues, inserting the DNA into a prokaryotic or eukaryotic expression vector, and then introducing the expression vector into a prokaryote or eukaryote to express the diabody.

"dsFv" is obtained by replacing one amino acid residue in each of VH and VL with a cysteine residue, and then connecting the substituted polypeptides via a disulfide bond between the two cysteine residues. The amino acid residues to be replaced with a cysteine residue can be selected based on three-dimensional structure prediction of the antibody in accordance with known methods (Protein Engineering, 7, 697 (1994)).

The dsFv of the present disclosure can be produced by the following steps: obtaining cDNAs encoding the VH and VL of the monoclonal antibody of the present disclosure, constructing a DNA encoding the dsFv, inserting the DNA into a prokaryotic or eukaryotic expression vector, and then introducing the expression vector into a prokaryote or eukaryote to express the dsFv.

The "CDR-containing peptide" is constituted by incorporating one or more regions in the CDRs of VH or VL. Peptides containing multiple CDRs can be linked directly or via a suitable peptide linker.

The CDR-containing peptide of the present disclosure can be produced by the following steps: constructing DNA encoding the CDRs of VH and VL of the monoclonal antibody in the present disclosure, inserting the DNA into a prokaryotic expression vector or a eukaryotic expression vector, the expression vector is then introduced into prokaryotes or eukaryotes to express the peptide. The CDR-containing peptide can also be produced by a chemical synthesis method, such as Fmoc method or tBoc method.

As used in the present disclosure, the term "framework (FR)" refers to a part of the variable domain, either VL or VH, which serves as a scaffold for the antigen binding loops (CDRs) of this variable domain. Essentially, it is a variable domain without CDRs.

The term "amino acid difference" refers to the difference(s) between a polypeptide and the variant(s) thereof at specific amino acid position(s) on the polypeptide fragment, wherein the variant(s) can be obtained by substituting, inserting or deleting amino acid(s) at specific position(s) on the polypeptide.

The term "epitope" refers to the sites on an antigen that specifically bind to an immunoglobulin or antibody. The epitope can be formed by adjacent amino acids, or by non-adjacent amino acids which have been brought to be closer due to tertiary folding of a protein. The epitope formed by adjacent amino acids is typically retained upon exposure to denaturing solvent, whereas the epitope formed by tertiary folding is typically absent after treatment with denaturing solvent. Epitopes typically include at least 3-15 amino acids in a unique spatial conformation. Methods for determining epitope are well known in the art, comprising immune-blotting and immune-precipitation assay, and the like. Methods for determining the spatial conformation of an epitope include techniques in the art and techniques described herein, such as X-ray crystallography and two-dimensional nuclear magnetic resonance, and the like.

The term "specifically binds to" used in present invention refers to the binding of an antibody to an epitope on a predetermined antigen. Typically, the antibody binds to a predetermined antigen with an equilibrium dissociation constant ($K_D$) of approximately less than $10^{-7}$ M or even less, and the affinity of the antibody for binding to the predetermined antigen is at least two times higher than that for binding to non-specific antigens (such as BSA) other than the predetermined antigen or closely-related antigens, as measured in an instrument via surface plasmon resonance (SPR) technique, wherein the recombinant human OX40 is used as an analyte while the antibody is used as a ligand. The term "an antibody recognizing an antigen" can be used interchangeably herein with the term "an antibody specifically binding to . . . ".

The term "KD" refers to the dissociation equilibrium constant for particular antibody-antigen interaction. Typically, the antibody of the present disclosure binds to human OX40 with a dissociation equilibrium constant (KD) of less than about $10^{-7}$M, for example, less than about $10^{-8}$M, $10^{-9}$M or $10^{-10}$M or even less; for example, as determined by Surface Plasma Resonance (SPR) technology in Biacore instrument.

When the term "competition" is used in the context of antigen-binding proteins (e.g., neutralizing antigen-binding proteins or neutralizing antibodies) that compete for the same epitope, it means that competition occurs between the antigen-binding proteins, which is determined by an assay in which: an antigen binding protein to be tested (e.g., an antibody or an antigen binding fragment thereof) prevents or inhibits (e.g., reduces) the specific binding of a reference antigen binding protein (e.g., a ligand or reference antibody) to a common antigen (e.g., a OX40 antigen or fragment thereof). Numerous types of competitive binding assays are available to determine whether an antigen-binding protein competes with another. These assays are, for example, solid phase direct or indirect radioimmunoassay (MA), solid phase direct or indirect enzyme immunoassay (EIA), Sandwich competition assay (see, e.g., Stahli et al, 1983, Methods in Enzymology 9: 242-253); solid phase direct biotin-avidin EIA (see, e.g., Kirkland et al, 1986, J. Immunol. 137: 3614-3619), solid phase direct labeling assay, solid phase direct labeling sandwich assay (see, e.g., Harlow and Lane, 1988, Antibodies, A Laboratory Manual, Cold Spring Harbor Press); solid phase direct labeling RIA with I-125 label (see, e.g., Morel et al, 1988, Molec. Immunol. 25: 7-15); and direct labeling RIA (Moldenhauer et al, 1990, Scand. J. Immunol. 32: 77-82). Typically, the assay involves the use of a purified antigen capable of binding to both an unlabeled test antigen binding protein and a labeled reference antigen binding protein (the antigen is loaded on a solid surface or cell surface). Competitive inhibition is determined by measuring the amount of label bound to the solid surface or to the cell surface in the presence of the test antigen-binding protein. Usually, the test antigen-binding protein is present in excess. Antigen-binding proteins identified by competitive assay (competitive antigen-binding protein) includes: antigen-binding proteins that bind to the same epitope as the reference antigen-binding protein; and antigen-binding proteins that bind to an epitope that is sufficiently close to the epitope to which the reference antigen-binding protein binds, where the two epitopes spatially interfere with each other to hinder the binding. Additional details regarding methods for determining competitive binding are provided in the examples herein. Typically, when a competitive antigen-binding protein is present in excess, it will inhibit (e.g., reduce) at least 40-45%, 45-50%, 50-55%, 55-60%, 60-65%, 65-70%, 70-75% or even more of the specific binding of the reference antigen-binding protein to the common antigen. In certain cases, the binding is inhibited by at least 80-85%, 85-90%, 90-95%, 95-97% or even more.

The term "cross-reaction" refers to the ability of the antibody of the present invention to bind to OX40 from different species. For example, an antibody of the present invention that binds to human OX40 can also bind to OX40 from another species. Cross-reactivity is measured by detecting the specific reactivity with purified antigen in binding assays (e.g., SPR and ELISA), or by detecting the binding or functional interaction with cells physiologically expressing OX40. Methods for determining cross-reactivity include standard binding assays as described herein, such as surface plasmon resonance analysis (SPR), or flow cytometry.

The term "inhibition" or "blocking" are used interchangeably, and covers both partial and complete inhibition/blocking.

The term "inhibition of growth" (e.g., when applied to cells) is intended to refer to any measurable decrease in cell growth.

The terms "inducing an immune response" and "enhancing an immune response" are used interchangeably, and refer to an immune response against the stimulation of a specific antigen (i.e, passive or adaptive). The term "induction" in the context of inducing CDC or ADCC refers to the stimulation of a specific direct cell killing mechanism.

"Antibody-dependent cell-mediated cytotoxicity" or "ADCC" refers to such a form of cytotoxicity, wherein the secretory immunoglobulins binding to Fc receptors (FcR) present on certain cytotoxic cells (such as NK cells, neutrophils, and macrophages) make these cytotoxic effector cells specifically bind to antigen-carrying target cells, and then kill the target cells by cytotoxins. The main cells (NK cells) that mediate ADCC express FcγRIII alone, while monocytes express FcγRI, FcγRII, and FcγRIII. FcR expression on hematopoietic cells is summarized in Table 3 on page 464 in Ravetch and Kinet, Annu. Rev. Immunol. 9:457-92 (1991). In order to evaluate the ADCC activity of the molecule of interest, an in vitro ADCC assay can be performed, such as that described in U.S. Pat. Nos. 5,500,362 5,821,337 or 6,737,056 (Presta). The effector cells useful for such assays include PBMC and NK cells. Alternatively, the ADCC activity of the molecule of interest can be assessed in vivo, for example in an animal model such as that disclosed in Clynes et al. PNAS (USA) 95:652-656 (1998). In addition, the Fc segment of IgG can be modified to reduce or eliminate the ADCC effect of antibodies. The modification refers to mutations in the heavy chain constant region of the antibody, such as mutations selected from the group consisting of N297A, L234A, L235A of IgG1; IgG2/4 chimera, F235E of IgG4, and L234A/E235A mutation.

The term "complement dependent cytotoxicity" or "CDC" refers to the lysis of target cells in the presence of complement. The classical pathway of complement activation is initiated by the binding of the first component of the complement system (C1q) to an antibody (of the appropriate subclass), which has bound to its cognate antigen. To assess complement activation, a CDC assay can be performed, for example as described in Gazzano-Santoro et al., J. Immunol. Methods 202:163 (1996). Polypeptide variants having modified Fc region amino acid sequence(s) (polypeptides with variant Fc region(s)) as well as having increased or decreased C1q-binding ability are described in, for example, U.S. Pat. No. 6,194,551B1 and WO 1999/51642. See also, for example, Idusogie et al., J. Immunol. 164: 4178-4184 (2000).

As used in the present disclosure, the term "nucleic acid molecule" refers to DNA molecule and RNA molecule. A nucleic acid molecule may be a single-stranded or double-stranded, but in particular double-stranded DNA. A nucleic acid is considered to be "operably linked", when it is placed into a functional relationship with another nucleic acid sequence. For instance, a promoter or enhancer is operably linked to an encoding sequence, when it has effect on the transcription of the sequence.

The term "vector" refers to a nucleic acid molecule capable of delivering another nucleic acid to which it has been linked. In one embodiment, the vector is a "plasmid," which refers to a cyclic double-stranded DNA loop into which additional DNA segment(s) may be ligated. In another embodiment, the vector is a viral vector, wherein additional DNA segments may be ligated into the viral genome. The vectors disclosed herein are capable of self-replicating in the host cell into which they are introduced (e.g., bacterial vectors having a bacterial replication origin and episomal mammalian vectors), or may be integrated into the genome of a host cell upon introduction into the host cell, and thereby are replicated along with the genome of the host (e.g., non-episomal mammalian vectors).

Methods for producing and purifying antibodies and antigen-binding fragments thereof are well known in the art, for example, A Laboratory Manual for Antibodies, Cold Spring Harbor Laboratory Press, Cold Spring Harbor, New York, chapters 5-8 and 15. For example, mice can be immunized with human OX40 or fragments thereof, and the resulting antibodies can then be renatured, purified, and sequenced for amino acid sequences by using conventional methods well known in the art. Antigen-binding fragments can also be prepared by conventional methods. The antibodies or antigen binding fragments thereof of the present disclosure are engineered to insert one or more human FR regions onto non-human CDR regions. Human FR germline sequences can be obtained from ImMunoGeneTics (IMGT) website http://imgt.cines.fr, or from The Immunoglobulin Facts Book, 2001 ISBN012441351, by aligning against the IMGT human antibody variable germline gene database using MOE software.

The antibodies or the antigen-binding fragments in the present disclosure may be prepared and purified using conventional methods. For example, cDNA sequences encoding a heavy chain and a light chain may be cloned and recombined into GS expression vector. The recombinant immunoglobulin expression vector then may be stably transfected into CHO cells. As a more recommended method in the art, mammalian expression system may result in glycosylation of antibodies, typically at the highly conserved N-terminus in the Fc region. Stable clones may be obtained through expression of an antibody specifically binding to human antigen. Positive clones may be expanded in a serum-free culture medium for antibody production in bioreactors. Culture medium, into which an antibody has been secreted, may be purified and collected by conventional techniques. The antibody may be subjected to filtration and concentration using common techniques. Soluble mixtures and multimers may be effectively removed by common techniques, such as molecular sieve or ion exchange. The obtained product shall be immediately frozen, for example at −70° C., or may be lyophilized.

The monoclonal antibody (mAb) refers to an antibody obtained from a single clone of cell strain which is but not limited to eukaryotic, prokaryotic, or phage clone of cell strain. Monoclonal antibodies and antigen-binding fragment thereof can be obtained, for example, by hybridoma technologies, recombinant technologies, phage display technologies, synthetic technologies (e.g., CDR-grafting), or other technologies known in the art.

The term "host cell" refers to a cell into which an expression vector has been introduced. Host cells may include microorganisms (such as bacteria), plants or animal cells. Bacteria susceptible to be transformed include members of the Enterobacteriaceae, such as *Escherichia coli* or *Salmonella*; Bacillaceae, such as *Bacillus subtilis; Pneumococcus; Streptococcus* and *Haemophilus influenzae*. Suitable microorganisms include *Saccharomyces cerevisiae* and *Pichia pastoris*. Suitable animal host cell lines include CHO (Chinese Hamster Ovary Cell Line), NS0 and 293 cells.

"Conservative modification" or "conservative replacement or substitution" means the substitution of other amino acids showing similar characteristics (such as charge, side chain size, hydrophobicity/hydrophilicity, main chain conformation and rigidity, etc) for the amino acids in a protein, such that the modification can be frequently performed without changing the biological activity of the protein. Those skilled in the art know that, generally, single amino acid substitution in a non-essential region of a polypeptide does not substantially change the biological activity (see for example, Watson et al. (1987) Molecular Biology of the Gene, The Benjamin/Cummings Pub. Co., Page 224 (4th edition)). In addition, the substitution of amino acids with similar structure or function is unlikely to result in the loss of biological activity.

"Effective amount" involves an amount sufficiently to ameliorate or prevent a symptom or sign of a medical symptom or condition. Effective amount also means an amount sufficiently to allow or facilitate diagnosis. An effective amount for a particular patient or veterinary subject may vary depending on factors such as the condition being treated, the general health of the patient, the route and dosage of administration and the severity of side effects. An effective amount can be the maximal dosage or dosing protocol that avoids significant side effects or toxic effects.

"Exogenous" refers to substances that are produced outside an organism, cell, or human body, depending on the context.

"Endogenous" refers to substances that are produced within an organism, cell, or human body, depending on the context.

The "mutated sequence" mentioned in the present disclosure refers to a nucleotide sequence and amino acid sequence having various percentage sequence identity to those of the present disclosure, after modifying the nucleotide sequence and amino acid sequence of the present disclosure by appropriate substitution, insertion or deletion. The sequence identity may be at least 85%, 90% or 95%, non-limiting examples include 85%, 86%, 87%, 88%, 89%, 90%, 91%, 92%, 93%, 94%, 95%, 96%, 97%, 98%, 99% and 100%. Sequence comparison between two sequences and determination of identity percent can be performed using the BLASTN/BLASTP algorithm available on the National Center For Biotechnology Institute website, with default settings.

As used in the present disclosure, "homology" or "identity" refers to a sequence similarity between two polynucleotide sequences or between two polypeptide sequences. When a position in both of the two sequences to be compared is occupied by the same base or amino acid monomer subunit, e.g., when a position in each of two DNA molecules is occupied by adenine, then the molecules are homologous at that position. The percent of homology between two sequences is a function of the number of matching or homologous positions shared by the two sequences divided by the number of all positions to be compared and then multiplied by 100. For example, when two sequences are optimally aligned, if 6 out of 10 positions in the two sequences are matched or homologous, then the two sequences are known as 60% homologous; if 95 out of 100 positions in the two sequences are matched or homologous, then the two sequences are known as 95% homologous. Generally, two sequences are compared when the alignment provides the maximum homology percentage.

As used in the present disclosure, the expressions "cell," "cell line," and "cell culture" are used interchangeably and all such designations involve progeny thereof. Thus, "transformant" and "transformed cell" include the primary subject cells and culture derived therefrom, regardless of the number of passages. It should be also understood that all progeny may not be precisely identical in the aspect of DNA content, due to intended or unintended mutations. Mutant progeny exhibiting the same function or biological activity as screened for the originally transformed cells are included. Where distinct designations are mentioned, it will be clearly understood according to the context.

As used in the present disclosure, "polymerase chain reaction" or "PCR" refers to a procedure or technique in which minute amounts of a specific portion of nucleic acid, RNA and/or DNA, are amplified as described in, e.g., U.S. Pat. No. 4,683,195. Generally, sequence information at the terminus of or beyond the region of interest needs to be available, such that oligonucleotide primers can be designed; these primers will be identical or similar in sequence to the complementary strand of the template to be amplified. The 5' terminus nucleotides of the two primers can be identical to the ends of the material to be amplified. PCR can be used to amplify specific RNA sequences, specific DNA sequences from total genome and cDNA transcribed from total cellular RNA, bacteriophage or plasmid sequences, etc. See generally Mullis et al. (1987) Cold Spring Harbor Symp. Ouant. Biol. 51:263; Erlich editor, (1989) PCR TECHNOLOGY (Stockton Press, NY). The PCR used in the present disclosure is considered to be one example (but not the only one) of polymerase reaction methods for amplifying a nucleic acid sample to be testes. The method comprises the use of nucleic acid sequences known as primers in combination with nucleic acid polymerase to amplify or generate a specific portion of nucleic acid.

"Optional" or "optionally" means that the event or circumstance that follows may (but does not necessarily) occur, and the description includes the instances where the event or circumstance does or does not occur. For example, "optionally contains 1-3 antibody heavy chain variable region(s)" means the antibody heavy chain variable region(s) with specific sequence can be, but need not be, present.

"Pharmaceutical composition" refers to a mixture containing one or more antibodies or the antigen binding fragments thereof according to the present disclosure, and other chemical components, such as physiologically/pharmaceutically acceptable carriers or excipients. The pharmaceutical composition aims at promoting the administration to an organism, facilitating the absorption of the active component and thereby exhibiting a biological effect.

The term "cancer" refers to or describes a physiological condition in mammals, characterized by unregulated cell growth. Examples of cancer include, but are not limited to, carcinoma, lymphoma, blastoma, sarcoma, and leukemia or lymphoid malignancies. More particular examples of such cancers include, but are not limited to, squamous cell carcinoma (e.g., epithelial squamous cell carcinoma), lung cancer (including small cell lung cancer, non-small cell lung cancer, adenocarcinoma, and squamous cell carcinoma of the lung), peritoneal cancer, hepatocellular carcinoma, gastric carcinoma (including gastrointestinal cancer and gastrointestinal stromal cancer), pancreatic cancer, glioblastoma, cervical cancer, ovarian cancer, liver cancer, bladder cancer, urethral cancer, liver tumor, breast cancer, colon cancer, rectum cancer, colorectal cancer, endometrial cancer or uterine cancer, salivary gland cancer, kidney cancer, prostate cancer, vulvar cancer, thyroid cancer, anal cancer, penile cancer, melanoma, superficial spreading melanoma, malignant freckle mole melanoma, acral melanoma, nodular melanoma, multiple myeloma and B-cell lymphoma, chronic lymphocytic leukemia (CLL), acute lymphoblastic leukemia (ALL), hairy cell leukemia, chronic myeloblastic leukemia, and post-transplant lymphoproliferative disorder (PTLD), as well as abnormal blood vessel proliferation associated with phakomatoses, edema (such as those associated with brain tumors) and Meigs syndrome, brain tumor and brain cancer, and head and neck cancer and related metastases thereof.

In certain embodiments, cancers suitable to be treated by the OX40 antibody or the fragment thereof in the present disclosure include breast cancer, colorectal cancer, rectal cancer, non-small cell lung cancer, glioblastoma, non-Hodgkin's lymph Tumor (NHL), renal cell carcinoma, prostate cancer, liver cancer, pancreatic cancer, soft tissue sarcoma, Kaposi's sarcoma, carcinoid carcinoma, head and neck cancer, ovarian cancer, mesothelioma, and multiple Myeloma. In some embodiments, the cancer is selected from the group consisting of: non-small cell lung cancer, glioblastoma, neuroblastoma, melanoma, breast cancer (e.g. triple negative breast cancer), gastric carcinoma, colorectal cancer (CRC), and hepatocellular carcinoma. Also, in some embodiments, cancer is selected from the group consisting of: non-small cell lung cancer, colorectal cancer, glioblastoma, and breast cancer (e.g. triple negative breast cancer), including metastases of those cancers.

The terms "cell proliferative disorder" and "proliferative disorder" refer to disorders associated with a certain degree of abnormal cell proliferation. In one embodiment, the cell proliferative disorder refers to cancer.

The term "tumor" refers to all neoplastic cell growth and proliferation, regardless of malignant or benign, and all pre-cancerous and cancerous cells and tissues.

The terms "cancer", "cancerous", "cell proliferative disorder", "proliferative disorder" and "tumor" are not mutually exclusive when referred to in the present disclosure.

"Administration", "administering" and "treatment", when applied to an animal, human, subject, cell, tissue, organ or biological fluid, refers to contacting an exogenous pharmaceutical, therapeutic, diagnostic agent, or composition with the animal, human, subject, cell, tissue, organ or biological fluid. "Administration", "administering" and "treatment" can refer to such as therapeutic, pharmacokinetic, diagnostic, research and experimental methods. Treatment of a cell involves contacting a reagent with a cell, as well as contacting a reagent with a fluid wherein said fluid is in contact with the cell.

"Administration", "administering" and "treatment" also mean in vitro and ex vivo treatment of e.g. a cell, by using a reagent, diagnostic, binding composition, or by using another cell. "Treatment" when applied to a human, veterinary or a research subject, refers to therapeutic treatment, prophylactic or preventative measures, research as well as diagnostic applications.

"To treat" means internal or external administration of a therapeutic agent (such as a composition comprising any of the antibodies or antigen-binding fragment thereof of the present disclosure; or a nucleic acid molecule encoding the antibody or antigen-binding fragment thereof) to a patient having one or more disease or symptom for which the therapeutic agent was known to show therapeutic activity. Typically, the therapeutic agent is administered in an amount effective to alleviate one or more disease or symptom in the treated patient or population, either by inducing the regression of such symptom(s), or by inhibiting the progression of such symptom(s) to any clinically measurable degree. The amount of a therapeutic agent that is effective to alleviate any particular disease or symptom (also referred to "therapeutically effective amount") may vary according to factors such as the disease state, age and weight of the patient, and the ability of the medicament to elicit a desired effect in the patient. Whether a disease symptom has been alleviated can be assessed by any clinical measurement typically used by physicians or other skilled healthcare providers to assess the severity or progression status of that symptom. While the embodiment of the present disclosure (e.g., a treatment method or article of manufacture) may not be effective in alleviating each disease symptom of interest, it should alleviate the target disease symptom(s) of interest in a statistically significant number of subjects as determined by any statistical test known in the art such as Student's t-test, chi-square test, U-test according to Mann and Whitney, Kruskal-Wallis test (H-test), Jonckheere-Terpstra-test and Wilcoxon-test.

The term "prevention of cancer" refers to delaying, inhibiting or preventing the onset of cancer in mammals; the initiation of the development of cancer or tumor has not been confirmed in the mammals, but the mammals have been identified to be susceptible to the cancer by for example genetic screening or other methods. The term also includes the treatment of a mammal suffering from precancerous condition in order to prevent the precancerous condition from progressing towards malignant tumor or even to achieve regression.

DETAILED DESCRIPTION OF THE INVENTION

Hereinafter, the present disclosure is further described with reference to the examples. However the scope of the present disclosure is not limited thereto. In the examples, where specific conditions are not described, the experiments are generally conducted under conventional conditions as described in Antibodies, A Laboratory Manual and Molecular Cloning Manual, by Cold Spring Harbor, or under conditions proposed by manufacturers of the material or product. Where the source of the reagents is not specifically given, the reagents are commercially available.

EXAMPLE 1

Preparation of Antibodies

The library of anti-human OX40 monoclonal antibodies was generated by immunizing mice. Experimental mice of the BalB/C and A1J strains (Center for Comparative Medicine, Yangzhou University, Animal Production License Number; SOCK(Jiangsu)2017-007), female, 10-week old.

Immune antigen was human OX40 recombinant protein with Fc tag (OX40-Fc: OX40 Leu29-Ala216 (Accession #NP_003318), fused with Fc), and was purchased from Acro Biosystems under catalog number #OX40-H5255, expressed in HEK293, and then purified according to conventional method.

OX40-Fc was emulsified with Freund's adjuvant: Freund's complete adjuvant (sigma-aldrich, F5881-10ML) was used for the first immunization, and Freund's incomplete adjuvant (sigma-aldrich, F5506-10ML) was used for the reset of booster immunizations. The ratio of antigen to adjuvant was 1:1, and 25 µg protein/200 µl/mouse was injected for each immunization. In detail, Day 1 The first immunization with complete Freund's adjuvant
Day 21 The second immunization with incomplete Freund's adjuvant
Day 35 The third immunization with incomplete Freund's adjuvant
Day 42 Blood sampling and serum titer test
Day 49 The fourth immunization with incomplete Freund's adjuvant
Day 56 Blood sampling and serum titer test.

The antibody titer in mouse serum and the neutralizing activity of blocking the binding of OX40/OX40L were determined with mouse serum by ELISA method as described in Example 2. The mice with strong serum titer, affinity and ability for blocking ligand binding were selected for a final immunization and then were sacrificed. The spleen cells were fused with SP2/0 myeloma cells (ATCC® CRL-1581™) and innoculated onto a plate to obtain hybridomas. Target hybridomas were selected by indirect ELISA, capture ELISA and cell-based functional screening as shown in Example 2, and monoclonal antibody strains were established by limited dilution method.

The established 19 strains of OX40 mouse monoclonal antibodies were produced by serum-free expression, and purified mouse monoclonal antibodies were obtained by protein A affinity chromatography. Hybridoma cells secreting activated anti-OX40 antibody were selected by indirect ELISA, capture ELISA and cell functional activity screening. The brief procedure of functional screening was as follows: GS-H2/OX40 stable cell line was cultivated (purchased from Genscript, cat #M00608). Diluted antibody to be tested and OX40L (Sino Biological, 13127-H04H) solution were prepared, and added into GS-H2/OX40 cells at logarithmic growth phase. After cultivation was finished, the cell supernatant was collected, and the content of IL-8 in the supernatant was measured (using human IL-8 kit, Cisbio, cat #62IL8PEB). The antibody GPX4 (prepared with reference to 1A7. gr.1 in the patent application WO2015153513) was used as a positive control in the test, and hIgG (prepared in the laboratory) was used as a negative control.

According to cell functional activity, 10 strains with high activity were selected for gene cloning and sequencing. The total RNAs were extracted from cells by conventional RNA extraction technology, and then the PCR products of the variable regions of the monoclonal antibodies were obtained by reverse transcription polymerase chain reaction (RT-PCR). The PCR products were resolved and recovered by agarose gel, then cloned into a gene vector which was then transformed into E.coli. Several transformed colonies were randomly selected, and the variable regions of monoclonal antibodies were amplified by PCR for gene sequencing. The corresponding sequences of the obtained exemplary murine monoclonal antibodies are shown below.

The heavy and light variable region sequences of the murine monoclonal antibody m4B5 are as follows:

m4B5 heavy chain variable region:
SEQ ID NO: 1
QVQLKQSGPGLVQPSQSLSITCTVSGFSLTSYGLHWFRQSPGKGLEWLGV
IWSGGSTDYNAAFISRLSISKDDSKSQVFFKMNSLQADDTAIYYCAREEY
DVWGTGTTVTVSS;

m4B5 light chain variable region:
SEQ ID NO: 2
DIQMTQTASSLSASLGDRVTISCRASQDISNYLNWYQQKPDGTVKLLIYY
TSRLHSGVPSRFSGSGSGTDYSLTISNLEQEDVATYFCQQGNTLPWTFGG
GTKLEIK.

The sequences of the CDR regions of murine monoclonal antibody m4B5 are shown in Table 1:

TABLE 1

| CDR region sequences of murine monoclonal antibody m4B5 | | |
|---|---|---|
| Name | Sequence | SEQ ID NO |
| HCDR1 | SYGLH | SEQ ID NO: 3 |
| HCDR2 | VIWSGGSTDYNAAFIS | SEQ ID NO: 4 |
| HCDR3 | EEYDV | SEQ ID NO: 5 |
| LCDR1 | RASQDISNYLN | SEQ ID NO: 6 |
| LCDR2 | YTSRLHS | SEQ ID NO: 7 |
| LCDR3 | QQGNTLPWT | SEQ ID NO: 8 |

The heavy and light chain variable region sequences of the murine monoclonal antibody m2G3 are as follows:

m2G3 heavy chain variable region:
SEQ ID NO: 9
QVQLKESGPGLVASSQSLSITCTVSGFSLSRYSVHWVRQPPGKGLEWLGM
IWDGGNTDYNSALKSRLSISKDNSKSQVFLKMNSLQTDDTAMYYCARNPL
YFSYAMDYWGQGTSVTVSS;

m2G3 light chain variable region:
SEQ ID NO: 10
DIQMTQSTSSLSASLGDRVTISCRASQDISNYLNWYQQKPDGTVKLLIIY
TSRLQSGVPSRFSGSGSGTDYSLTISNLEQEDIATYFCQQVNTFPFTFGS
GTKLEIK.

The sequences of the CDR regions of murine monoclonal antibody m2G3 are shown in Table 2:

TABLE 2

| CDR region sequences of murine monoclonal antibody m2G3 | | |
|---|---|---|
| Name | Sequence | SEQ ID NO |
| HCDR1 | RYSVH | SEQ ID NO: 11 |
| HCDR2 | MIWDGGNTDYNSALKS | SEQ ID NO: 12 |
| HCDR3 | NPLYFSYAMDY | SEQ ID NO: 13 |

TABLE 2-continued

CDR region sequences of murine monoclonal antibody m2G3

| Name  | Sequence   | SEQ ID NO      |
|-------|------------|----------------|
| LCDR1 | RASQDISNYLN | SEQ ID NO: 14 |
| LCDR2 | YTSRLQS    | SEQ ID NO: 15  |
| LCDR3 | QQVNTFPFT  | SEQ ID NO: 16  |

EXAMPLE 2

Identification and Screening of Antibodies by ELISA

Indirect ELISA Method:

20×coating buffer was diluted to 1× by using deionized water. 100 μL of human OX40-His antigen (Acro biosytems, OXL-H52Q8) prepared by using 1×coating buffer (carbonate buffer) to a final concentration of 2 μg/mL was added to each well, and incubated at 4° C. overnight or 37° C. for 2 h. The plate was washed once with PBST, 200 μL of blocking solution (PBST containing 5% skimmed milk) was added to each well, incubated at 37° C. for 2 h, and the plate was washed for 4 times with PB ST. 100 μL of the diluted primary antibody was added to each well (the antibody to be tested was 5-fold diluted from the concentration of 10000 ng/ml, resulting in seven gradients, namely 10000 ng/ml, 2000 ng/ml, 400 ng/ml, 80 ng/ml, 16 ng/ml, 3.2 ng/ml, and 0.64 ng/ml, blank wells merely contained dilution solution, i.e., 2.5% skimmed milk in PBST), and incubated at 37° C. for 40 minutes. The plate was washed for 4 times with PBST, and the enzyme-labeled secondary antibody (HRP-labeled goat anti-mouse IgG, purchased from Jackson Immunoresearch, Cat #115036071 or HRP-labeled goat anti-human IgG, purchased from Jackson Immunoresearch, Cat #109036098) was diluted with PBST buffer; 100 μL was added to each well and incubated at 37° C. for 40 min. The plate was washed for 4 times with PBST, and 100 μL TMB developing solution was added to each well, incubated for 3-15 minutes in dark at room temperature, and 50 μl stop solution (1M sulfuric acid) was added to each well. The parameters were set for the microplate reader, the OD value was read at 450-630 nm, and the test data were saved.

Capture ELISA:

20×PBS buffer was diluted to 1× with deionized water. 100 μL of GAM secondary antibody (Jackson Immunoresearch, 115-006-071) prepared with 1×PBS to a final concentration of 2 μg/mL was added to each well, and incubated at 4° C. overnight or 37° C. for 2 h; the plate was washed once with PBST, 200 μL blocking solution (PBST containing 5% skimmed milk) was added to each well, incubated at 37° C. for 2 h, and the plate was washed with PBST for 4 times. 100 μL of the diluted primary antibody was added to each well (the antibody to be tested was 5-fold diluted from the concentration of 10000 ng/ml, resulting in seven gradients, namely 10000 ng/ml, 2000 ng/ml, 400 ng/ml, 80 ng/ml, 16 ng/ml, 3.2 ng/ml, and 0.64 ng/ml, blank wells merely contained dilution solution, i.e., 2.5% skimmed milk in PBST), and incubated at 37° C. for 40 minutes. The plate was washed for 4 times with PBST, human OX40-FC-biotin (Acro biosystem, OX0-H5255, labeled biotin) was diluted with 2.5% skimmed milk in PBST, 100 μl was added to each well, incubated at 37° C. for 40 min, and the plate was washed for 4 times with PB ST. 100 μL TMB developing solution was added to each well, incubated for 3-15 minutes in dark at room temperature, 50 μl stop solution (1M sulfuric acid) was added to each well. The parameters were set for the microplate reader, the OD value was read at 450-630 nm, and the test data were saved.

Blocking ELISA of Ligand Binding:

20×coating buffer was diluted to 1× by using deionized water, 100 μL of OX40L-His antigen (Acro biosytems, OXL-H52Q8) prepared by using 1×coating buffer (carbonate buffer) to a final concentration of 2 μg/mL was added to each well, and incubated at 4° C. overnight or 37° C. for 2 h. The plate was washed once with PBST, 200 μL of blocking solution (PBST containing 5% skimmed milk) was added to each well, incubated at 37° C. for 2 h, and the plate was washed for 4 times with PBST; the mouse serum/antibody was gradient-diluted with pre-prepared 200 ng/ml human OX40-Fc solution (prepared in 2.5% skimmed milk), and then pre-incubated at room temperature for 40 minutes, then added to the blocked OX40L plate at 100 μL/well, and incubated for 40 min; the plate was washed for 4 times with PBST; HRP-labeled goat anti-human secondary antibody (GAH-HRP, Jackson Immunoresearch, 109-035-006) was diluted with PBST buffer; 100 μL was added to each well and incubated at 37° C. for 40 min. The plate was washed for 4 times with PBST, and 100 μL TMB developing solution was added to each well, incubated for 3-15 minutes in dark at room temperature, and 50 μl stop solution (1M sulfuric acid) was added to each well. The parameters were set for the microplate reader, the OD value was read at 450-630 nm, and the test data were saved.

EXAMPLE 3

Construction and Expression of Anti-OX40 Recombinant Chimeric Antibody

The murine antibody m2G3 and m4B5 heavy chain variable region (VH) in combination with human immunoglobulin heavy chain constant region, and light chain variable region (VL) in combination with human immunoglobulin Kappa light chain constant region were separately cloned into eukaryotic expression vector, which was then transfected into cells to produce mouse-human chimeric antibodies.

The heavy chain vector was designed as follows: signal peptide+heavy chain variable region sequence+human IgG1 constant region sequence.

The light chain vector was designed as follows: signal peptide+light chain variable region sequence+human Kappa constant region sequence.

The above sequences were inserted into pCEP4 vector (Thermofisher, V04450). After obtaining the vector plasmid, the plasmid was extracted and was delivered to sequencing for verification. The qualified plasmid was transfected into human 293F cells with PEI and cultured continuously, and the 293F cells were cultivated in serum-free medium (Shanghai OPM biosciences, OPM-293 CD03) to reach logarithmic growth phase for cell transfection. 21.4 μg of chimeric antibody light chain plasmid and 23.6 μg of chimeric antibody heavy chain plasmid were dissolved in 10 ml Opti-MEM®I Reduced Serum Medium (GIBCO, 31985-070) and mixed well, then 200 μg PEI was added, mixed well, and incubated at room temperature for 15 min, and added into 50 mL cells. Cell culture conditions: 5% $CO_2$, 37° C., 125 rpm/min. During the culture period, medium supplementary was added on day 1 and day 3 until the cell viability was less than 70%, and the cell supernatant was collected and centrifuged. After centrifugation and filtration, the cell culture solution was loaded onto affinity column for antibody purification, the column was washed with phosphate buffer, eluted with glycine-hydrochloric acid buffer (pH 2.7, 0.1M Gly-HCl), neutralized with 1M Tris hydrochloric acid pH 9.0, and dialyzed against phosphate buffer, and purified chimeric antibodies Ch2G3 and Ch4B5 were finally obtained.

EXAMPLE 4

In Vitro Binding Affinity and Kinetics Test

Figure 1B:
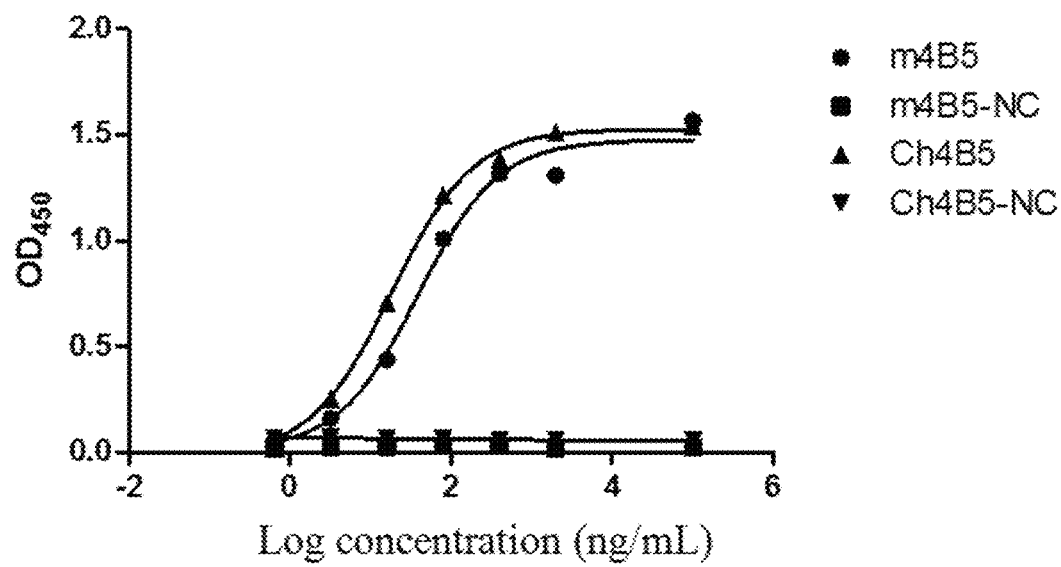

The affinity to human OX40 was detected on murine antibodies and chimeric antibodies (method steps were the same as described in Example 2), and the results are shown in FIG. 1A and FIG. 1B. m2G3-NC (-NC represents negative control), Ch2G3-NC, m4B5-NC and Ch4B5-NC were negative controls, which share the same constant regions as that used in m2G3, Ch2G3, m4B5, and Ch4B5, respectively, however, the variable regions thereof do not recognize OX40.

The results show that the chimeric antibodies Ch2G3 and Ch4B5 have high affinity to human OX40.

EXAMPLE 5

In Vitro Cell Test of Reporter Gene for Anti-OX40 Antibody

The well-plate was coated with anti-CD3 antibody (Chempartner, A05-001), placed at 4° C. overnight and washed for 3 times with PBS; Jurkat-NF-Kb luc-hOX40 cells (ATCC, TIB-152 stable cell line constructed by Shanghai ChemPartner) and Raji cells (ATCC, CCL-86) were harvested, resuspended and mixed. 50 µl/well of the diluted antibody to be tested and 50 µl/well of the mixed two types of cells were added into the plate, and the plate was incubated at 37° C. in 5% $CO_2$ incubator for 5 hours. 100 µl One-Glo™ luciferase reagent (Promega, Cat #E6120) was added to each well, and incubated at room temperature for more than 3 minutes. The luminescent signal was measured on the instrument, RLU reading was recorded. The results are shown in Table 3.

TABLE 3

Results of in vitro activation of reporter gene by anti-OX40 antibodies

| Antibody | $EC_{50}$ (nM) |
| --- | --- |
| Ch2G3 | 0.6371 |
| Ch4B5 | 0.5589 |

The results show that the chimeric antibodies Ch2G3 and Ch4B5 can effectively activate the reporter gene.

EXAMPLE 6 humanization Test of Murine Antibody

In order to reduce the possible immunogenicity, murine antibodies were humanized. The heavy chain variable region (VH) and light chain variable region (VL) of the chimeric antibody were respectively subjected to site-directed amino acid mutations in the FR region (framework region). According to different combinations of amino acid mutations, different humanized antibody heavy chains and light chains were designed, and plasmids encoding different light/heavy chain combinations were transfected into cells to produce humanized antibodies. Briefly, as follows:

Firstly, the expression vector was designed:

The heavy chain vector was designed as follows: signal peptide+mutated heavy chain variable region sequence+human IgG1 constant region sequence.

The light chain vector was designed as follows: signal peptide+mutated light chain variable region sequence+human Kappa constant region sequence.

The above sequences were separately inserted into pCEP4 vector (Thermofisher, V04450). The expression vectors were synthesized by a third-party gene synthesis company according to the above design. After obtaining the vector plasmid, the plasmid was extracted and sent to sequencing for verification. The qualified plasmid was transfected into human 293F cells with PEI and cultured continuously, and the 293F cells were cultivated in serum-free medium (Shanghai OPM biosciences, OPM-293 CD03) to reach logarithmic growth phase for cell transfection. 21.4 µg of the plasmid encoding the humanized antibody light chain and 23.6 µl of the plasmid encoding the humanized antibody heavy chain were dissolved in 10 ml Opti-MEM®I Reduced Serum Medium (GIBCO, 31985-070) and mixed well, then 200 µg PEI was added, and mixed well, incubated at room temperature for 15 min, and added to 50 mL cells.

Cell culture conditions: 5% $CO_2$, 37° C., 125 rpm/min. During the culture period, medium supplementary was added on day 1 and day 3 until the cell viability was less than 70%, and the cell supernatant was collected and centrifuged. After centrifugation and filtration, the cell culture solution was loaded onto affinity column for antibody purification, the column was washed with phosphate buffer, eluted with glycine-hydrochloric acid buffer (pH 2.7, 0.1M Gly-HCl), neutralized with 1M Tris hydrochloric acid pH 9.0, and dialyzed against phosphate buffer, and purified humanized antibodies were finally obtained.

The sequences of the humanized variable regions are as follows:

```
>hu2G3 VH1
                                        SEQ ID NO: 17
QVQLQESGPGLVKPSETLSLTCTVSGYSISRYSVHWVRQPPGKGLEWIGM

IWDGGNTDYNSALKSRFTISRDNSKNTLYLQMNSLRAEDTAVYYCARNPL

YFSYAMDYWGQGTLVTVSS;

>hu2G3 VH2
                                        SEQ ID NO: 18
QVQLQESGPGLVKPSETLSLTCTVSGGSISRYSVHWIRQPPGKGLEWIGM

IWDGGNTDYNSALKSRVTISVDTSKNQFSLKLSSVTAADTAVYYCARNPL

YFSYAMDYWGQGTLVTVSS;

>hu2G3 VL1
                                        SEQ ID NO: 19
DIQMTQSPSSLSASVGDRVTITCRASQDISNYLNWYQQKPDQSPKLLIIY

TSRLQSGVPSRFSGSGSGTDYTLTISSLQPEDFATYYCQQVNTFPFTFGQ

GTKLEIK;
```

-continued

\>hu2G3 VL2

SEQ ID NO: 20

*DIQMTQSPSSLSASVGDRVTITC*RASQDISNYLN*WYQQKPGKAPKLLIYY*

TSRLQS*GVPSRFSGSGSGTDYILTISSLQPEDFATYYC*QQVNTFPFT*FGQ*

*GTKLEIK*.

Note:
The order is FR1-CDR1-FR2-CDR2-FR3-CDR3-FR4, the italic sequence represents FR, and underlined sequence represents CDR.

The designed variable regions of humanized antibody were combined into different antibodies as follows:

TABLE 4

Humanized m2G3 antibody and the heavy and light chain variable regions thereof

| Antibody | VH | VL |
|---|---|---|
| 2G3-hu1 | hu2G3 VH1 | hu2G3 VL1 |
| 2G3-hu2 | hu2G3 VH2 | hu2G3 VL1 |
| 2G3-hu3 | hu2G3 VH1 | hu2G3 VL2 |
| 2G3-hu4 | hu2G3 VH2 | hu2G3 VL2 |

Note:
2G3-hu1 means that the heavy chain variable region of the humanized antibody 2G3-hu1 is hu2G3 VH1, the light chain variable region is hu2G3 VL1, and other antibodies can be interpretated in similar way.

The sequences of the humanized variable regions of m4B5 are as follows:

hu4B5 VL0:

SEQ ID NO: 21
*DIQMTQSPSSLSASVGDRVTITC*RASQDISNYLN*WYQQKPGKVPKLLIYY*

TSRLHS*GVPSRFSGSGSGTDFTLTISSLQPEDVATYYC*QQGNTLPWT*FGG*

*GTKVEIK*;

hu4B5 VL1:

SEQ ID NO: 22
*DIQMTQSPSSLSASVGDRVTITC*RASQDISNYLN*WYQQKPGKVPKLLIYY*

TSRLHS*GVPSRFSGSGSGTDYTLTISSLQPEDVATYYC*QQGNTLPWT*FGG*

*GTKVEIK*;

hu4B5 VL2:

SEQ ID NO: 23
*DIQMTQSPSSLSASVGDRVTITC*RASQDISNYLN*WYQQKPGGVPKLLIYY*

TSRLHS*GVPSRFSGSGSGTDYTLTISSLQPEDVATYYC*QQGNTLPWT*FGG*

*GTKVEIK*;

hu4B5 VL3:

SEQ ID NO: 24
*DIQMTQSPSSLSASVGDRVTITC*RASQDISNYLN*WYQQKPGGVPKLLIYY*

TSRLHS*GVPSRFSGSGSGTDYILTISSLQQEDVATYYC*QQGNTLPWT*FGG*

*GTKVEIK*;

hu4B5 VL4:

SEQ ID NO: 25
*DIQMTQSPSSLSASVGDRVTITC*RASQDISNYLN*WYQQKPGGTVKLLIYY*

TSRLHS*GVPSRFSGSGSGTDYTLTISSLQPEDVATYFC*QQGNTLPWT*FGG*

*GTKVEIK*;

hu4B5 VH0:

SEQ ID NO: 26
*QVQLQESGPGLVKPSETLSLTCTVSGFSLT*SYGLH*WIRQPPGKGLEWIG*V

IWSGGSTDYNAAFIS*RVTISVDTSKNQFSLKLSSVTAADTAVYYC*AREEY

DV*WGQGTTVTVSS*;

hu4B5 VH1:

SEQ ID NO: 27
*QVQLQESGPGLVKPSETLSLTCTVSGFSLT*SYGLH*WIRQPPGKGLEWIG*V

IWSGGSTDYNAAFIS*RVTISKEDSKNQFSLKLSSVTAADTAVYYC*AREEY

DV*WGQGTTVTVSS*;

hu4B5 VH2:

SEQ ID NO: 28
*QVQLQESGPGLVKPSETTSLTCTVSGFSLT*SYGLH*WIRQPPGKGLEWIG*V

IWSGGSTDYNAAFIS*RVTISKEDSKSQVSLKLSSVTAADTAVYYC*AREEY

DV*WGQGTTVTVSS*;

hu4B5 VH3:

SEQ ID NO: 29
*QVQLKESGPGLVKPSETTSLTCTVSGFSLT*SYGLH*WFRQPPGKGLEWIG*V

IWSGGSTDYNAAFIS*RVTISKEDSKSQVSLKLSSVTAADTAVYYC*AREEY

DV*WGQGTTVTVSS*;

hu4B5 VH4:

SEQ ID NO: 30
*QVQLKESGPGLVKPSETTSLTCTVSGFSLT*SYGLH*WFRQPPGKGLEWLG*V

IWSGGSTDYNAAFIS*RLTISKEDSKSQVSLKLSSVTAADTAVYYC*AREEY

DV*WGQGTTVTVSS*.

The designed variable regions of humanized antibody were combined into different antibodies as follows:

TABLE 5 m4B5 humanized antibody and the corresponding
heavy and light chain variable regions thereof

| Heavy/Light chain variable region | hu4B5 VH0 | hu4B5 VH1 | hu4B5 VH2 | hu4B5 VH3 | hu4B5 VH4 |
|---|---|---|---|---|---|
| hu4B5VL0 | hu4B5-V1 | hu4B5-V2 | hu4B5-V3 | hu4B5-V4 | hu4B5-V5 |
| hu4B5VL1 | hu4B5-V6 | hu4B5-V8 | hu4B5-V9 | hu4B5-V10 | hu4B5-V11 |
| hu4B5VL2 | hu4B5-V15 | hu4B5-V16 | hu4B5-V17 | hu4B5-V7 | hu4B5-V12 |
| hu4B5VL3 | hu4B5-V18 | hu4B5-V19 | hu4B5-V20 | hu4B5-V21 | hu4B5-V13 |
| hu4B5VL4 | hu4B5-V22 | hu4B5-V23 | hu4B5-V24 | hu4B5-V25 | hu4B5-V14 |

Note:
Hu4B5 V1 means that the heavy chain variable region of the humanized antibody hu4B5 V1 is hu4B5 VH0, the light chain variable region is hu4B5 VL0, and other antibodies can be interpretated in similar way.

In order to obtain a better humanized modified m2G3 antibody, the amino acid sequence of hu2G3 VH1 was subjected to mutation. The sequence of the heavy chain variable region after mutation is as follows:

hu2G3 VH1.1
SEQ ID NO: 31
QVQLQESGPGLVKPSETLSLTCTVSGYSISRYSVHWVRQPPGKGLEWIGM

IWDGGNTDYNAALKSRFTISRDNAKNTLYLQMNSLRAEDTAVYYCARNPL

YFSYAMDYWGQGTLVTVSS;

>hu2G3 VH1.2
SEQ ID NO: 32
QVQLQESGPGLVKPSQTLSLTCTVSGFSLSRYSVHWVRQPPGKGLEWIGM

IWDGGNTDYAAPVKGRFTISRDDSKNTLYLQMNSLKTEDTAVYYCARNPL

YFSYAMDYWGQGTLVTVSS.

The HCDR2 sequence obtained after mutation is as follows:

TABLE 6

| HCDR2 sequence obtained after mutation | | |
|---|---|---|
| Name | Sequence | SEQ ID NO |
| HCDR2$_{v1}$ | MIWDGGNTDYNAALKS | SEQ ID NO: 33 |
| HCDR2$_{v2}$ | MIWDGGNTDYAAPVKG | SEQ ID NO: 34 |

The heavy chain variable regions hu2G3 VH1.1 and hu2G3 VH1.2 were combined with the light chain variable region hu2G3 VL to form new optimized humanized antibodies, see Table 7.

TABLE 7

The light/heavy chain variable regions of the new
humanized hu2G3 antibody obtained after mutation

| Antibody | VH | VL |
|---|---|---|
| 2G3 | hu2G3 VH1.1 | hu2G3 VL1 |
| 2G3-hu5 | hu2G3 VH1.1 | hu2G3 VL2 |
| 2G3-hu6 | hu2G3 VH1.2 | hu2G3 VL1 |
| 2G3-hu7 | hu2G3 VH1.2 | hu2G3 VL2 |

The humanized antibodies described above were tested for affinity (refer to the capture ELISA in Example 2), and the test results showed that the humanized molecules can bind to OX40.

The affinity evaluation (capture ELISA) results for exemplary m2G3 and the humanized antibody thereof are shown in Table 8:

TABLE 8

| Antibody affinity | | | | | | |
|---|---|---|---|---|---|---|
| Antibody | m2G3 | 2G3-hu1 | 2G3-hu6 | 2G3-hu2 | 2G3-hu7 | 2G3-hu4 |
| $EC_{50}$ (μg/mL) | 0.867 | 0.886 | 0.82 | 1.60 | 0.743 | 2.269 |

The capture ELISA test results for exemplary m4B5 and the modified antibodies thereof are shown in Table 9:

TABLE 9

| Antibody affinity | | | | | | |
|---|---|---|---|---|---|---|
| Antibody | m4B5 | Ch4B5 | hu4B5-v1 | hu4B5-v7 | hu4B5-v10 | hu4B5-v14 |
| $EC_{50}$ (μg/mL) | 0.58 | 0.208 | 0.59 | 0.254 | 0.76 | 0.536 |

The light chain variable region sequence as described above was combined with the light chain constant region sequence to form the final light chain sequences, and the heavy chain variable region sequence as described above was combined with the heavy chain constant region to form the final heavy chain sequences. The specific light and heavy chain constant regions are not limited to the antibody constant regions disclosed in the present disclosure. Other light and heavy chain constant regions and the mutants thereof known in the art can also be used to increase the performance of the antibody.

The exemplary constant regions are as follows:

IgG1 heavy chain constant region:
SEQ ID NO: 35
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSREEMTKNQVSLTC

LVKGFYPSDIAVEWESNGQPENNYKTTPPVLDSDGSFFLYSKLTVDKSRW

QQGNVFSCSVMHEALHNHYTQKSLSLSPGK;

-continued kappa light chain constant region:
SEQ ID NO: 36
RTVAAPSVFIFPPSDEQLKSGTASVVCLLNNFYPREAKVQWKVDNALQSG
NSQESVTEQDSKDSTYSLSSTLTLSKADYEKHKVYACEVTHQGLSSPVTK
SFNRGEC.

The amino acid sequences of exemplary full-length 2G3 and hu4B5-V7 (also known as 4B5) antibody are as follows:

2G3 heavy chain:
SEQ ID NO: 37
QVQLQESGPGLVKPSETLSLTCTVSGYSISRYSVHWVRQPPGKGLEWIGM
IWDGGNTDYNAALKSRFTISRDNAKNTLYLQMNSLRAEDTAVYYCARNPL
YFSYAMDYWGQGTLVTVSSASTKGPSVFPLAPSSKSTSGGTAALGCLVKD
YFPEPVTVSWNSGALTSGVHTFPAVLQSSGLYSLSSVVTVPSSSLGTQTY
ICNVNHKPSNTKVDKKVEPKSCDKTHTCPPCPAPELLGGPSVFLFPPKPK
DTLMISRTPEVTCVVVDVSHEDPEVKFNWYVDGVEVHNAKTKPREEQYNS
TYRVVSVLTVLHQDWLNGKEYKCKVSNKALPAPIEKTISKAKGQPREPQV
YTLPPSREEMTKNQVSLTCLVKGFYPSDIAVEWESNGQPENNYKTTPPVL
DSDGSFFLYSKLTVDKSRWQQGNVFSCSVMHEALHNHYTQKSLSLSPGK;

2G3 light chain:
SEQ ID NO: 38
DIQMTQSPSSLSASVGDRVTITCRASCIDISNYLNWYQQKPDQSPKLLIT
YTSRLQSGVPSRFSGSGSGTDYTLTISSLQPEDFATYYCQQVNTFPFTFG
QGTKLEIKRTVAAPSVFIFPPSDEQLKSGTASVVCLLNNFYPREAKVQWK
VDNALQSGNSQESVTEQDSKDSTYSLSSTLTLSKADYEKHKVYACEVTHQ
GLSSPVTKSFNRGEC;

4B5 heavy chain:
SEQ ID NO: 39
QVQLKESGPGLVKPSETLSLTCTVSGFSLTSYGLHWFRQPPGKGLEWIGV
IWSGGSTDYNAAFISRVTISKEDSKSQVSLKLSSVTAADTAVYYCAREEY
DVWGQGTTVTVSSASTKGPSVFPLAPSSKSTSGGTAALGCLVKDYFPEPV
TVSWNSGALTSGVHTFPAVLQSSGLYSLSSVVTVPSSSLGTQTYICNVNH
KPSNTKVDKKVEPKSCDKTHTCPPCPAPELLGGPSVFLFPPKPKDTLMIS
RTPEVTCVVVDVSHEDPEVKFNWYVDGVEVHNAKTKPREEQYNSTYRVVS
VLTVLHQDWLNGKEYKCKVSNKALPAPIEKTISKAKGQPREPQVYTLPPS
REEMTKNQVSLTCLVKGFYPSDIAVEWESNGQPENNYKTTPPVLDSDGSF
FLYSKLTVDKSRWQQGNVFSCSVMHEALHNHYTQKSLSLSPGK;

4B5 light chain:
SEQ ID NO: 40
DIQMTQSPSSLSASVGDRVTITCRASQDISNYLNWYQQKPGGVPKLLIYY
TSRLHSGVPSRFSGSGSGTDYTLTISSLQPEDVATYYCQQGNTLPWTFGG
GTKVEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQG
LSSPVTKSFNRGEC.

The positive control GPX4 was prepared with reference to 1A7. gr.1 taught in the patent WO2015153513, and the heavy and light chain amino acid sequences thereof are as follows:

GPX4 heavy chain:
SEQ ID NO: 41
EVQLVQSGAEVKKPGASVKVSCKASGYTFTDSYMSWVRQAPGQGLEWIGD
MYPDNGDSSYNQKFRERVTITRDTSTSTAYLELSSLRSEDTAVYYCVLAP
RWYFSVWGQGTLVTVSSASTKGPSVFPLAPSSKSTSGGTAALGCLVKDYF
PEPVTVSWNSGALTSGVHTFPAVLQSSGLYSLSSVVTVPSSSLGTQTYIC
NVNHKPSNTKVDKKVEPKSCDKTHTCPPCPAPELLGGPSVFLFPPKPKDT
LMISRTPEVTCVVVDVSHEDPEVKFNWYVDGVEVHNAKTKPREEQYNSTY
RVVSVLTVLHQDWLNGKEYKCKVSNKALPAPIEKTISKAKGQPREPQVYT
LPPSREEMTKNQVSLTCLVKGFYPSDIAVEWESNGQPENNYKTTPPVLDS
DGSFFLYSKLTVDKSRWQQGNVFSCSVMHEALHNHYTQKSLSLSPGK;

GPX4 light chain:
SEQ ID NO: 42
DIQMTQSPSSLSASVGDRVTITCRASQDISNYLNWYQQKPGKAPKLLIYY
TSRLRSGVPSRFSGSGSGTDFTLTISSLQPEDFATYYCQQGHTLPPTFGQ
GTKVEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQG
LSSPVTKSFNRGEC.

EXAMPLE 7

Test of In Vitro Binding Affinity and Kinetics for Humanized Antibody

The Biacore method is a well-recognized method for objectively detecting the affinity and kinetics between proteins. We used Biacore T200 (GE) to analyze the OX40 antibodies to be tested of the present invention in order to characterize affinity and binding kinetics.

Using the kit provided by Biacore, the recombinant anti-OX40 antibody to be tested of the present invention was covalently connected to the CM5 (GE) chip by NHS standard amino coupling method. A series of concentration gradients of human OX40-His protein (sinobiological #10481-H08H) diluted in the same buffer were then loaded into each cycle at a flow rate of 30 μL/min. After loading, the chip was regenerated using regeneration reagent provided in the kit. The antigen-antibody binding kinetics was traced for 3 minutes, and the dissociation kinetics was traced for 10 minutes. The resulting data were analyzed by using BIAevaluation software (GE) with 1:1 (Langmuir) binding model. The ka ($k_{on}$), kd ($k_{off}$) and $K_D$ values of the chimeric antibodies determined by this method are shown in the table below.

TABLE 10

Results showing in vitro binding affinity of humanized antibodies

| Antibody to be tested | ka (1/Ms) | kd (1/s) | $K_D$ (M) |
|---|---|---|---|
| 2G3 | 4.371E+05 | 2.023E−03 | 4.628E−09 |
| 4B5 | 1.314E+05 | 3.694E−04 | 2.812E−09 |

The results show that both 2G3 and 4B5 can effectively bind to OX40.

EXAMPLE 8

ELISA Test of the Blocking of the OX40-OX40L Binding by Antibodies

The well-plate was coated with the OX40 ligand (Acrobiosystem, OXL-H52Q8), blocked, added the gradient-diluted antibody to be tested (the antibody was diluted in a solution comprising human Bio-OX40-FC (Acrobiosystem, OX40-H5255, labeled with biotin), pre-incubated for 40 minutes, and then added into the plate), incubated for 40 minute, and washed. SA-HRP (Jackson Immunoresearch, 016-030-084) was then added and incubated for 40 min. The developing solution and stop solution were added, and the OD value was measured. The results are shown in the table below.

TABLE 11

Test results of the blocking of the OX40-OX40L binding by antibody

| Antibody | 2G3 | 4B5 |
|---|---|---|
| $IC_{50}$ (nM) | 1.88 | 0.725 |

The results show that both 2G3 and 4B5 can block the binding of OX40 to OX40L.

EXAMPLE 9

Activity Data of Humanized Antibody

The well-plate was coated with anti-CD3 antibody (Chempartner, A05-001), placed at 4° C. overnight and washed for 3 times with PBS; Jurkat-NF-Kb luc-hOX40 cells (ATCC, TIB-152, a stable cell line constructed by Shanghai ChemPartner) and Raji cells (ATCC, CCL-86) were harvested. The two kinds of cells were re-suspended and mixed. 50 μl/well of the diluted antibody to be tested and 50 μl/well of the mixed two kinds of cells were added to the plate, and the plate was incubated at 37° C. in 5% $CO_2$ incubator for 5 hours. One-Glo™ luciferase reagent (Promega, Cat #E6120) was added to each well, and incubated at room temperature for more than 3 minutes. The luminescent signal was measured on the instrument, RLU reading was recorded. The results are shown in Table 12. The results show that both 2G3 and 4B5 can effectively activate the reporter gene.

TABLE 12

Test results of activation of reporter gene by humanized antibody

| Antibody | 2G3 | 4B5 |
|---|---|---|
| $EC_{50}$ (nM) | 2.294 | 0.3411 |

EXAMPLE 10

In vitro Cell Function Test

Figure 2:
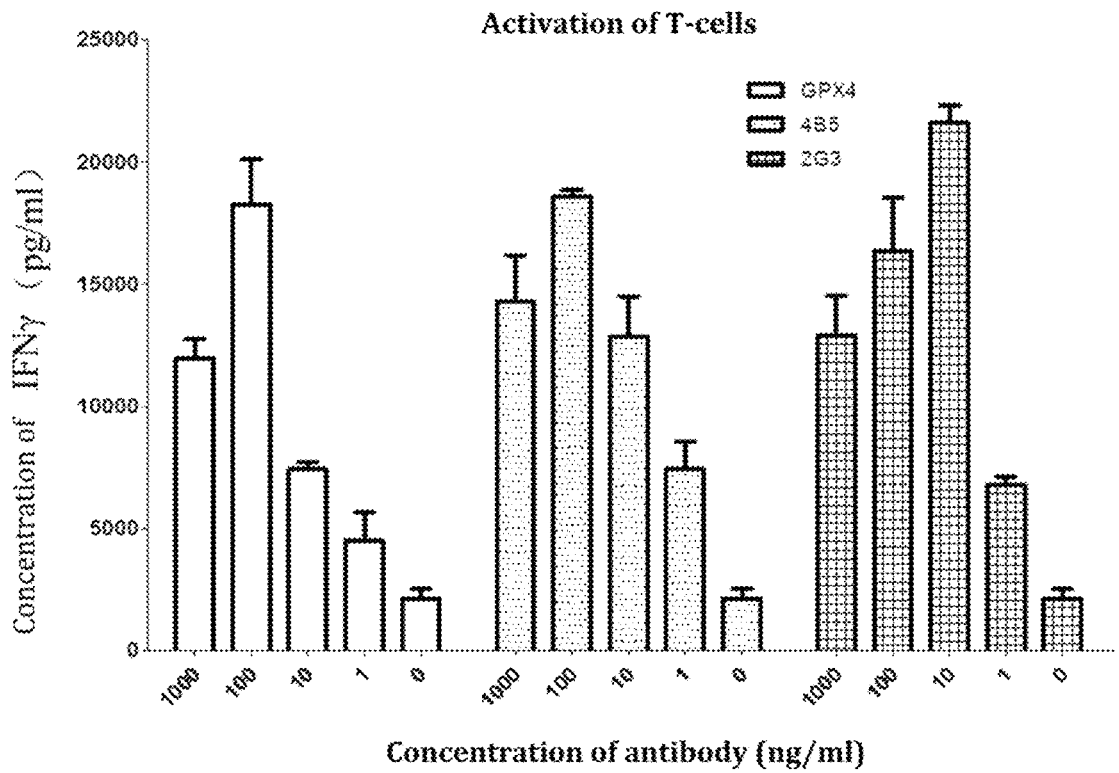
FIG. 2: Test showing the IFN-γ secreted in T cells stimulated by anti-OX40 antibody. The results show that the test OX40 antibody achieves the maximum stimulating effect at a concentration of 10 ng/mL.

CD4+ memory T cells were isolated and added together with the antibody to be tested to a 96-well plate coated with anti-CD3 antibody (Chempartner, A05-001), co-incubated at 37° C. for 72 hours, the supernatant was collected to detect IFN-γ. The results are shown in FIG. 2 and Table 13. The results show that GPX4, 4B5 and 2G3 can significantly enhance the release of IFN-γ, and 2G3 can achieve the maximum stimulating effect at 10 ng/mL.

TABLE 13

IFNγ (pg/mL) values corresponding to different antibodies

| Concentration of antibody (ng/mL) | GPX | 4B5 | 2G3 |
|---|---|---|---|
| 1000 | 11965 ± 783 | 14286 ± 1893 | 12892 ± 1648 |
| 100 | 18261 ± 1847 | 18582 ± 269 | 16345 ± 2192 |
| 10 | 7420 ± 305 | 12844 ± 1657 | 21604 ± 717 |
| 1 | 4515 ± 1145 | 7413 ± 1149 | 6801 ± 333 |
| 0 |  | 2126 ± 402 |  |

Note:
The data were calculated as follows: mean +/− SEM (average +/− standard error of mean), N = 3 (three repeats).

EXAMPLE 11

Inhibition of the Tumor Cell Growth by Anti-OX40 Antibody

B-hTNFRSF4 (OX40) humanized mice (B-hTNFRSF4 (OX40) humanized mice, from Biocytogen Jiangsu Gene Biotechnology Co., Ltd.), female, 17 to 20 g, 6 to 7 week old.

The MC38 tumor cells 7 at logarithmic growth phase were collected (purchased from Nanjing Yinhe Biomedicine Co., Ltd.), the cell concentration was adjusted to $5 \times 10^6$/mL with PBS buffer, and 0.1 mL of cell suspension was inoculated to the flanks of OX40 mice. The mice were monitored after inoculation for the growth of tumors. On day 7 after inoculation, the average tumor volume in the flank of tumor-bearing mice reached 102.5 mm³. Mice were divided into groups according to the tumor size, administrated and monitored. The grouping information is shown in Table 14.

TABLE 14

Mouse grouping and schedule for administration dosage

| Administration group | Administration dosage (mg/kg) | Administration route | Administration frequency |
|---|---|---|---|
| Control (IgG1) | 3 | i.p. | Q3D × 6 |
| GPX4 | 3 | i.p. | Q3D × 6 |
| 2G3 | 0.3 | i.p. | Q3D × 6 |
| 2G3 | 1 | i.p. | Q3D × 6 |
| 2G3 | 3 | i.p. | Q3D × 6 |

The OX40 humanized antibody was tested for its inhibitory effect on the growth of MC38 colon cancer cell xenograft in mice.

Measurement of the tumor volume and the weight of tumor-bearing mice: tumor was measured twice a week using a caliper. The tumor volume was calculated according to the formula: $V=0.5 \ a \times b^2$, a and b represent the long diameter and wide diameter of the tumor, respectively; Tumor growth xenograft TGI (%)=[1−T/C]×100. The weight of all tumor-bearing mice was measured twice a week.

On day 20 after administration, the average tumor volume of IgG1 control group reached 1732.593 mm³; and the average tumor volume of the test compound 2G3 low-dose administration group (0.3 mg/kg), medium-dose administration group (2G3, 1 mg/kg) and high-dose administration group (2G, 3 mg/kg) reached 930.37 mm³, 303.49 mm³ and 155.79 mm³, respectively. The medium and high-dose group significantly inhibited the tumor growth, when compared with the control group (**P<0.01), and a preliminary dose-dependent relationship was observed, with the tumor growth inhibition rate of up to 49%, 88% and 97.0%, respectively. The average tumor volume in the 3 mg/kg GPX4 group was 362.47 mm$^3$, which was significantly different from that of control group, and 3 mg/kg GPX4 group also showed significant tumor growth inhibition (*P<0.05), with the tumor growth inhibition rate of up to 84%.

Figure 3A:
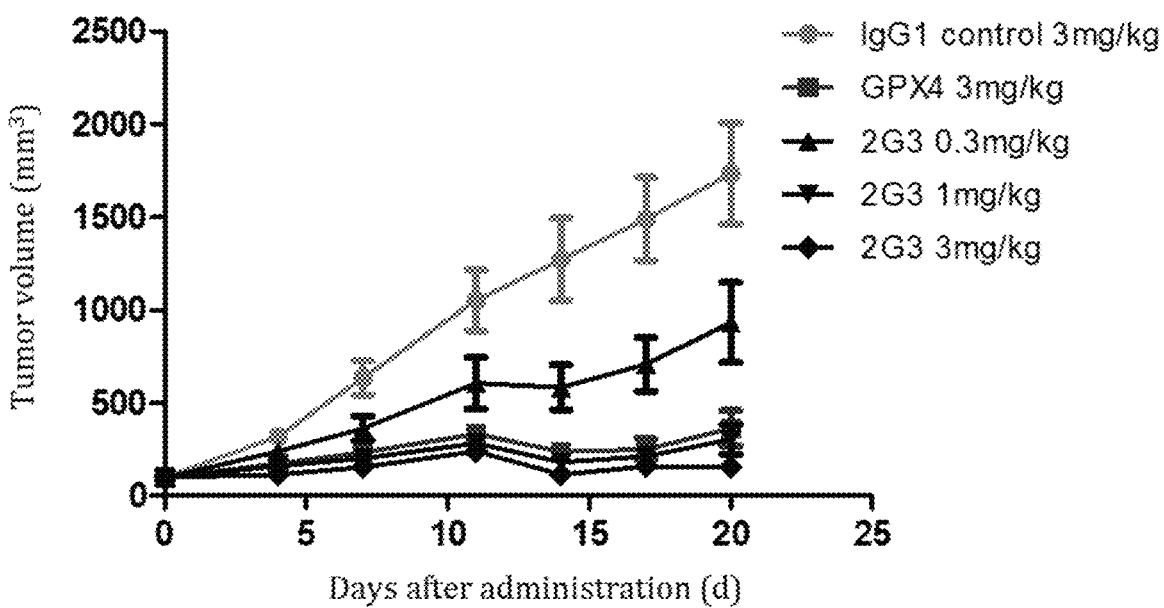
FIG. 3A to FIG. 3B: anti-tumor effect of anti-OX40 antibody in mice.
Figure 3B:
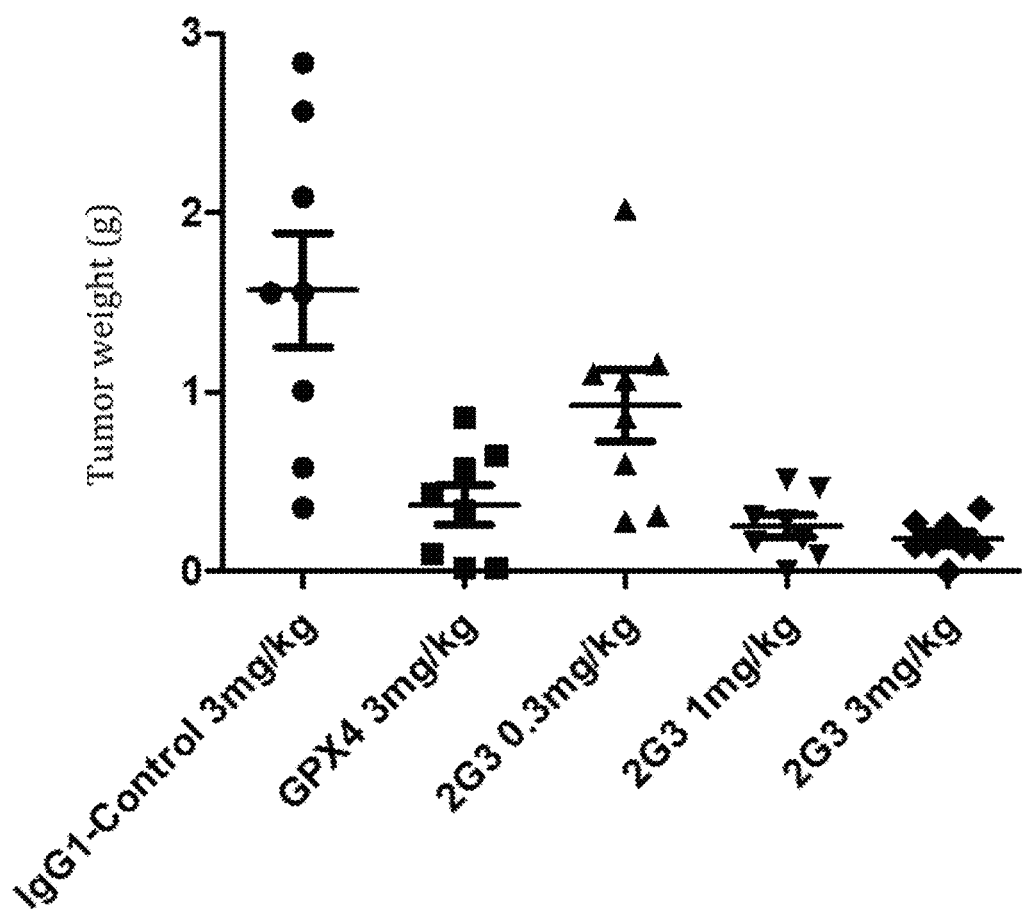

The test was ended on day 20 after administration. The results are shown in Table 15 and FIG. 3A and FIG. 3B. All the treated mice were euthanized, and the subcutaneous xenograft mass was removed from the tumor-bearing mice and weighed. The average weight of tumor mass in the control group was 1.568 g; as for the test compound 2G3 in the low-dose group (0.3 mg/kg), medium-dose group (1 mg/kg) and high-dose group (3 mg/kg), the average tumor weight reached 0.926 g, 0.251 g and 0.181 g, respectively; the medium and high-dose group significantly inhibited the tumor growth, when compared with the control group (P<0.01). Meanwhile, in the GPX4 (3 mg/kg) administration group, the average tumor weight was 0.372 g, which was significantly different from that of the control group, and GPX4 (3 mg/kg) administration group also showed a significant inhibitory effect on the growth of MC38 tumor cells (P<0.01).

During the test, there was no obvious abnormality in body weight of all treated tumor-bearing mice. At the same time, there were no obvious abnormal behaviors and other manifestations during the medicament treatment.

TABLE 15

In vivo anti-tumor effect in mice

|  | 2G3 | | | GPX4 | IgG1 |
|---|---|---|---|---|---|
| Dosage (mg/kg) | 0.3 | 1 | 3 | 3 | — |
| Tumor volume (mm$^3$) | 930.37 | 303.49 | 155.79 | 362.47 | 1732.59 |
| Tumor weight (g) | 0.926 | 0.251 | 0.181 | 0.372 | 1.568 |
| Tumor inhibitory rate (%) | 49 | 88 | 97 | 84 | — |

What is claimed is:

1. An anti-OX40 antibody or antigen-binding fragment thereof, wherein:
   the anti-OX40 antibody or antigen-binding fragment thereof comprises:
   i) HCDR1 as shown in SEQ ID NO: 11, HCDR2 as shown in SEQ ID NO: 33, SEQ ID NO: 12 or SEQ ID NO: 34, and HCDR3 as shown in SEQ ID NO: 13, and LCDR1, LCDR2 and LCDR3 as shown in SEQ ID NOs: 14, 15 and 16 respectively; or
   ii) HCDR1, HCDR2 and HCDR3 as shown in SEQ ID NOs: 11, 12 and 13 respectively, and LCDR1, LCDR2 and LCDR3 as shown in SEQ ID NOs: 14, 15 and 16 respectively.

2. The anti-OX40 antibody or antigen-binding fragment thereof according to claim 1, which is a murine antibody, chimeric antibody, humanized antibody or fragment thereof.

3. The anti-OX40 antibody or antigen-binding fragment thereof according to claim 1, further comprising a heavy chain variable region of human IgG1, IgG2, IgG3 or IgG4; wherein the antigen-binding fragment is selected from the group consisting of: Fab, Fab', Fv, scFv, and F(ab')2 fragment.

4. The anti-OX40 antibody or antigen-binding fragment thereof according to claim 1, wherein the antibody comprises a heavy chain constant region comprising human IgG1, IgG2, IgG3 or IgG4, and/or a light chain constant region comprising human kappa or lambda chain.

5. The anti-OX40 antibody or antigen-binding fragment thereof according to claim 4, wherein the amino acid sequence of the heavy chain constant region is as shown in SEQ ID NO: 35 or having at least 90% sequence identity to SEQ ID NO: 35, and the amino acid sequence of the light chain constant region is as shown in SEQ ID NO: 36 or having at least 90% sequence identity to SEQ ID NO: 36.

6. The anti-OX40 antibody or antigen-binding fragment thereof according to claim 1, wherein:
   the heavy chain variable region comprises:
   I) an amino acid sequence as shown in SEQ ID NO: 9 or having at least 95% sequence identity to SEQ ID NO: 9; or
   II) an amino acid sequence as shown in any one of SEQ ID NO: 17, 18, 31 and 32; or having at least 95% sequence identity to SEQ ID NO: 17, 18, 31 or 32;
   and/or, the light chain variable region comprises:
   I) an amino acid sequence as shown in SEQ ID NO: 10 or having at least 95% sequence identity to SEQ ID NO: 10; or
   II) an amino acid sequence as shown in any one of SEQ ID NO: 19 and 20; or
   having at least 95% sequence identity to SEQ ID NO: 19 or 20.

7. The anti-OX40 antibody or antigen-binding fragment thereof according to claim 6, wherein the anti-OX40 antibody or antigen-binding fragment thereof comprises:
   i) a heavy chain variable region as shown in SEQ ID NO: 9 and a light chain variable region as shown in SEQ ID NO: 10;
   ii) a heavy chain variable region as shown in SEQ ID NO: 17 or 18, and a light chain variable region as shown in SEQ ID NO: 19; or
   iii) a heavy chain variable region as shown in SEQ ID NO: 17 or 18, and a light chain variable region as shown in SEQ ID NO: 20.

8. The anti-OX40 antibody or antigen-binding fragment thereof according to claim 1, comprising:
   i) a heavy chain as shown in SEQ ID NO: 37 or having at least 85%, at least 90%, at least 95%, at least 98% or at least 99% sequence identity to SEQ ID NO: 37, and/or,
   a light chain as shown in SEQ ID NO: 38 or having at least 85%, at least 90%, at least 95%, at least 98% or at least 99% sequence identity to SEQ ID NO: 38.

9. A reagent, which comprises the anti-OX40 antibody or antigen-binding fragment thereof of claim 1.

10. A pharmaceutical composition, which comprises:
    a therapeutically effective amount of the anti-OX40 antibody or antigen-binding fragment thereof of claim 1; and
    one or more pharmaceutically acceptable carriers, diluents, buffers or excipients.

11. A polynucleotide encoding the anti-OX40 antibody or antigen-binding fragment thereof of claim 1.

12. A vector comprising the polynucleotide of claim 11.

13. A host cell comprising the vector of claim 12.

14. A method for preparing an anti-OX40 antibody or antigen-binding fragment thereof, comprising: cultivating the host cell of claim 13; recovering the anti-OX40 antibody or antigen-binding fragment thereof; optionally, purifying the anti-OX40 antibody or antigen-binding fragment thereof.

15. A method for detecting or measuring OX40, which comprises: a step of contacting the anti-OX40 antibody or antigen-binding fragment thereof of claim 1 with a biological sample.

16. A method for treating colon cancer, which comprises: administering a therapeutically effective amount of the anti-OX40 antibody or antigen-binding fragment thereof of claim 1 to a subject.

17. A method for enhancing an immune response in a human subject, which comprises: administering a therapeutically effective amount of the anti-OX40 antibody or the antigen-binding fragment thereof of claim 1 to a subject.

* * * * *